US006756520B1

(12) United States Patent
Krzysik et al.

(10) Patent No.: US 6,756,520 B1
(45) Date of Patent: Jun. 29, 2004

(54) HYDROPHILIC COMPOSITIONS FOR USE ON ABSORBENT ARTICLES TO ENHANCE SKIN BARRIER

(75) Inventors: Duane Gerard Krzysik, Appleton, WI (US); David Roland Otts, Appleton, WI (US); Beth Anne Lange, Appleton, WI (US); Brenda Marie Nelson, Appleton, WI (US); Earl David Brock, Kimberly, WI (US); Martha Lillian Tate, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 285 days.

(21) Appl. No.: 09/694,048

(22) Filed: Oct. 20, 2000

(51) Int. Cl.⁷ ............................................. A61F 13/15
(52) U.S. Cl. ..................... 604/360; 604/359; 604/367
(58) Field of Search .................. 604/359, 360, 604/364, 367, 304–308; 424/401, 65, 402, 404, 443, 445–449; 514/865, 847; 602/48

(56) References Cited

U.S. PATENT DOCUMENTS

| | | |
|---|---|---|
| 3,305,392 A | 2/1967 | Britt |
| 3,489,148 A | 1/1970 | Duncan et al. |
| 3,585,998 A | 6/1971 | Hayford et al. |
| 3,724,465 A | 4/1973 | Duchane |
| 3,756,238 A | 9/1973 | Hanke |
| 3,814,101 A | 6/1974 | Kozak |
| 3,821,350 A | 6/1974 | Suchane |
| 3,881,488 A | 5/1975 | Delanty et al. |
| 3,896,807 A | 7/1975 | Buchalter |
| 3,902,493 A | 9/1975 | Baier et al. |
| 4,040,857 A | 8/1977 | Lissant |
| 4,100,324 A | 7/1978 | Anderson et al. |
| 4,164,563 A | 8/1979 | Chang |
| 4,226,889 A * | 10/1980 | Yuhas ........................ 424/59 |

(List continued on next page.)

FOREIGN PATENT DOCUMENTS

| | | |
|---|---|---|
| CA | 2019557 A1 | 12/1990 |
| DE | 3536318 A1 | 4/1987 |
| DE | 41 36 540 A1 | 5/1992 |
| EP | 0 212 870 B1 | 7/1986 |
| EP | 0 613 675 A1 | 9/1994 |
| EP | 0 797 968 A1 | 10/1997 |
| EP | 0 808 151 B1 | 11/1997 |
| EP | 0 815 841 A1 | 1/1998 |
| EP | 0 875 233 A1 | 11/1998 |

(List continued on next page.)

OTHER PUBLICATIONS

Akin, Frank J.; Lemmen, Jac T.; Bozarth, Dena L.; Garofalo, Martin J.; and Grove, Gary L.; "A refined method to evaluate diapers for effectiveness in reducing skin hydration using the adult forearm," *Skin Research and Technology*, ISSN 0909–752X, 1997, pp. 173–176.

Berg, Ronald W., Ph.D; Milligan, Michael C., M.B.A.; and Sarbaugh, Frank C.; "Association of Skin Wetness and pH with Diaper Dermatitis," *Pediatric Dermatology*, Mar. 1994, vol. 11, No. 1, pp. 18–20.

(List continued on next page.)

*Primary Examiner*—John J. Calvert
*Assistant Examiner*—Jacqueline F Stephens
(74) *Attorney, Agent, or Firm*—Alyssa A. Dudkowski

(57) ABSTRACT

The present invention relates to compositions and absorbent articles including compositions for protecting and enhancing the barrier function of the skin. The compositions can be applied to the bodyfacing surfaces of absorbent articles so that the compositions come into contact with the skin. The compositions of the invention have improved stability on the bodyfacing surfaces after processing. The compositions of the invention provide several benefits including prevention and alleviation of skin irritations associated with the use of absorbent articles. The compositions can include hydrophilic solvents, high molecular weight polyethylene glycols, fatty alcohols, surfactants, natural fats, natural oils, sterols or sterol derivatives and emollients.

45 Claims, 3 Drawing Sheets

U.S. PATENT DOCUMENTS

| | | | |
|---|---|---|---|
| 4,273,786 A | 6/1981 | Kraskin | |
| 4,343,783 A | 8/1982 | Hooper et al. | |
| 4,355,020 A | 10/1982 | Kuy | |
| 4,355,046 A | 10/1982 | Suess | |
| 4,556,560 A | 12/1985 | Buckingham | |
| 4,604,313 A | 8/1986 | McFarland et al. | |
| 4,613,447 A | 9/1986 | Hara et al. | |
| 4,623,339 A | 11/1986 | Ciraldo et al. | |
| 4,634,438 A | 1/1987 | Sustmann et al. | |
| 4,634,439 A | 1/1987 | Sustmann et al. | |
| 4,637,820 A | 1/1987 | Marini et al. | |
| 4,655,756 A | 4/1987 | Fawkes | |
| 4,657,537 A | 4/1987 | Zimmerer | |
| 4,675,014 A | 6/1987 | Sustmann et al. | |
| 4,685,909 A | 8/1987 | Berg et al. | |
| 4,711,780 A | 12/1987 | Fahim | |
| 4,732,797 A | 3/1988 | Johnson et al. | |
| 4,738,678 A | 4/1988 | Paulis | |
| 4,753,643 A | 6/1988 | Kassai | |
| 4,753,647 A | 6/1988 | Curtis | |
| 4,760,096 A | 7/1988 | Sakai et al. | |
| 4,772,501 A | 9/1988 | Johnson et al. | |
| 4,790,836 A | 12/1988 | Brecher | |
| 4,790,840 A | 12/1988 | Cortina | |
| 4,798,603 A | 1/1989 | Meyer et al. | |
| 4,808,175 A | 2/1989 | Hansen | |
| 4,834,737 A | 5/1989 | Khan | |
| 4,861,405 A | 8/1989 | Kassai | |
| 4,882,204 A | 11/1989 | Tenenbaum | |
| 4,904,524 A * | 2/1990 | Yoh | 442/61 |
| 4,911,932 A | 3/1990 | Clum et al. | |
| 4,931,052 A | 6/1990 | Feldman | |
| 4,960,592 A | 10/1990 | Hagen et al. | |
| 4,970,220 A * | 11/1990 | Chaussee | 514/358 |
| 4,978,534 A | 12/1990 | Saitoh | |
| 4,990,144 A | 2/1991 | Blott | |
| 4,996,238 A | 2/1991 | Matravers | |
| 5,043,155 A | 8/1991 | Puchalski et al. | |
| 5,049,440 A | 9/1991 | Bornhoeft, III et al. | |
| 5,091,193 A | 2/1992 | Enjolras et al. | |
| 5,110,593 A | 5/1992 | Benford | |
| 5,139,790 A | 8/1992 | Snipes | |
| 5,141,803 A | 8/1992 | Pregozen | |
| 5,147,576 A | 9/1992 | Montague et al. | |
| 5,176,668 A | 1/1993 | Bernardin | |
| 5,176,672 A | 1/1993 | Bruemmer et al. | |
| 5,192,277 A | 3/1993 | Chung et al. | |
| 5,192,606 A | 3/1993 | Proxmire et al. | |
| 5,194,261 A | 3/1993 | Pichierri | |
| 5,232,691 A | 8/1993 | Lemole | |
| 5,244,668 A | 9/1993 | Snipes | |
| 5,306,486 A | 4/1994 | McCook et al. | |
| 5,336,212 A | 8/1994 | De Francesco | |
| 5,336,692 A | 8/1994 | Gans et al. | |
| 5,350,624 A | 9/1994 | Georger et al. | |
| 5,362,488 A | 11/1994 | Sibley et al. | |
| 5,364,382 A | 11/1994 | Latimer et al. | |
| 5,376,655 A | 12/1994 | Imaki et al. | |
| 5,384,125 A | 1/1995 | DiPippo et al. | |
| 5,409,903 A | 4/1995 | Polak et al. | |
| 5,436,007 A | 7/1995 | Hartung et al. | |
| 5,466,232 A | 11/1995 | Cadieux et al. | |
| 5,482,765 A | 1/1996 | Bradley et al. | |
| 5,486,166 A | 1/1996 | Bishop et al. | |
| 5,490,846 A | 2/1996 | Ellis et al. | |
| 5,496,298 A | 3/1996 | Kuepper et al. | |
| 5,509,915 A | 4/1996 | Hanson et al. | |
| 5,525,346 A | 6/1996 | Hartung et al. | |
| 5,533,990 A | 7/1996 | Yeo | |
| 5,569,230 A | 10/1996 | Fisher et al. | |
| 5,578,310 A | 11/1996 | M'Timkulu et al. | |
| 5,601,871 A | 2/1997 | Krzysik et al. | |
| 5,605,749 A | 2/1997 | Pike et al. | |
| 5,607,760 A | 3/1997 | Roe | |
| 5,607,980 A | 3/1997 | McAtee et al. | |
| 5,609,587 A | 3/1997 | Roe | |
| 5,614,293 A | 3/1997 | Krzysik et al. | |
| 5,618,529 A | 4/1997 | Pichierri | |
| 5,618,850 A | 4/1997 | Coury et al. | |
| 5,631,012 A | 5/1997 | Shanni | |
| 5,635,191 A | 6/1997 | Roe et al. | |
| 5,643,588 A | 7/1997 | Roe et al. | |
| 5,643,899 A | 7/1997 | Elias et al. | |
| 5,648,083 A * | 7/1997 | Blieszner et al. | 424/402 |
| 5,650,218 A | 7/1997 | Krzysik et al. | |
| 5,652,049 A | 7/1997 | Suzuki | |
| 5,652,194 A | 7/1997 | Dyer et al. | |
| 5,658,559 A | 8/1997 | Smith | |
| 5,665,368 A | 9/1997 | Lentini et al. | |
| 5,665,426 A * | 9/1997 | Krzysik et al. | 427/211 |
| 5,693,037 A | 12/1997 | Lee et al. | |
| 5,695,868 A | 12/1997 | McCormack | |
| 5,738,859 A | 4/1998 | Posner | |
| H1732 H | 6/1998 | Johnson | |
| 5,801,107 A | 9/1998 | Everhart et al. | |
| 5,830,487 A | 11/1998 | Klofta et al. | |
| 5,843,056 A | 12/1998 | Good et al. | |
| 5,849,314 A | 12/1998 | Dobkowski et al. | |
| 5,855,897 A | 1/1999 | Pelle | |
| 5,855,999 A | 1/1999 | McCormack | |
| 5,856,245 A | 1/1999 | Caldwell et al. | |
| 5,869,033 A | 2/1999 | Schulz | |
| 5,869,075 A | 2/1999 | Krzysik | |
| 5,869,172 A | 2/1999 | Caldwell | |
| 5,871,763 A * | 2/1999 | Luu et al. | 424/402 |
| 5,879,341 A | 3/1999 | Odorzynski et al. | |
| 5,891,126 A | 4/1999 | Osborn, III et al. | |
| 5,938,649 A | 8/1999 | Ducker et al. | |
| 5,944,705 A | 8/1999 | Ducker et al. | |
| 5,945,110 A | 8/1999 | Vianen et al. | |
| 5,951,990 A | 9/1999 | Ptchelintsev | |
| 5,989,577 A | 11/1999 | Hoath et al. | |
| 5,990,377 A | 11/1999 | Chen et al. | |
| 6,004,566 A | 12/1999 | Friedman et al. | |
| 6,031,147 A | 2/2000 | Gross | |
| 6,051,749 A | 4/2000 | Schulz | |
| 6,075,179 A | 6/2000 | McCormack et al. | |
| 6,093,869 A | 7/2000 | Roe et al. | |
| 6,100,442 A | 8/2000 | Samuelsson et al. | |
| 6,103,245 A | 8/2000 | Clark et al. | |
| 6,107,537 A | 8/2000 | Elder et al. | |
| 6,117,439 A | 9/2000 | Kake | |
| 6,118,041 A | 9/2000 | Roe et al. | |
| 6,120,488 A | 9/2000 | VanRijswijck et al. | |
| 6,136,332 A | 10/2000 | Grollier et al. | |
| 6,149,934 A | 11/2000 | Krzysik et al. | |
| 6,152,906 A | 11/2000 | Faulks et al. | |
| 6,153,209 A | 11/2000 | Vega et al. | |
| 6,156,024 A | 12/2000 | Schulte et al. | |
| 6,166,285 A | 12/2000 | Schulte et al. | |
| 6,183,766 B1 | 2/2001 | Sine et al. | |
| 6,217,890 B1 | 4/2001 | Paul et al. | |
| 6,238,682 B1 * | 5/2001 | Klofta et al. | 424/402 |
| 6,287,581 B1 | 9/2001 | Krzysik et al. | |
| 6,294,186 B1 | 9/2001 | Beerse et al. | |
| 6,316,030 B1 * | 11/2001 | Kropf et al. | 424/489 |
| 6,344,218 B1 | 2/2002 | Dodd et al. | |
| 6,433,244 B1 * | 8/2002 | Roe et al. | 604/361 |
| 2001/0006666 A1 | 7/2001 | Harbeck | |
| 2002/0086039 A1 * | 7/2002 | Lee et al. | 424/401 |

FOREIGN PATENT DOCUMENTS

| | | |
|---|---|---|
| EP | 0 922 452 A1 | 6/1999 |
| EP | 0 922 456 A1 | 6/1999 |
| EP | 1 057 476 A1 | 12/2000 |
| GB | 880276 | 10/1961 |
| GB | 884688 | 12/1961 |
| GB | 2 033 751 A | 5/1980 |
| GB | 2311727 A | 10/1997 |
| JP | 10-37070 | 2/1988 |
| WO | WO 90/12555 A1 | 11/1990 |
| WO | WO 92/09289 A1 | 6/1992 |
| WO | WO 93/16670 A1 | 9/1993 |
| WO | WO 93/21878 A1 | 11/1993 |
| WO | WO 94/09757 A1 | 5/1994 |
| WO | WO 94/09796 A1 | 5/1994 |
| WO | WO 95/19190 A1 | 7/1995 |
| WO | WO 96/16681 A1 | 6/1996 |
| WO | WO 96/16682 A1 | 6/1996 |
| WO | WO 97/05908 A2 | 2/1997 |
| WO | WO 97/05909 A2 | 2/1997 |
| WO | WO 97/38735 A1 | 10/1997 |
| WO | WO 97/38738 A1 | 10/1997 |
| WO | WO 98/00858 A1 | 1/1998 |
| WO | WO 98/03147 A1 | 1/1998 |
| WO | WO 98/47546 A1 | 10/1998 |
| WO | WO 98/55159 A2 | 12/1998 |
| WO | WO 99/12530 A1 | 3/1999 |
| WO | WO 99/13861 A1 | 3/1999 |
| WO | WO 99/26610 A1 | 6/1999 |
| WO | WO 99/26618 A1 | 6/1999 |
| WO | WO 99/26619 A1 | 6/1999 |
| WO | WO 99/45771 A1 | 9/1999 |
| WO | WO 99/45973 A1 | 9/1999 |
| WO | WO 99/45974 A1 | 9/1999 |
| WO | WO 99/45976 A1 | 9/1999 |
| WO | WO 99/46316 A1 | 9/1999 |
| WO | WO 00/38747 A2 | 7/2000 |
| WO | WO 00/64407 A1 | 11/2000 |
| WO | WO 00/64501 A1 | 11/2000 |
| WO | WO 00/64503 A1 | 11/2000 |
| WO | WO 00/69481 A1 | 11/2000 |
| WO | WO 00/69482 A1 | 11/2000 |
| WO | WO 00/69483 A1 | 11/2000 |
| WO | WO 00/69484 A1 | 11/2000 |
| WO | WO 00/71177 A1 | 11/2000 |

OTHER PUBLICATIONS

Imai, Satoshi and Kuwabara, Chihiro; Pigeon Co., Ltd., Ibaragi, Japan; "Infant Skin and Its Care," *Cosmetics & Toiletries*, vol. 107, Jul., 1992, pp. 85–86, 88–90.

Preston, Sandra L., PharmD & Bryant, Bobby G., MS, PharmD; "Etiology and Treatment of Diaper Dermatitis," *Hospital Pharmacy*, 1994, vol. 29, No. 12, pp. 1086–1088, 1097.

Sires, Ulrike I., MD & Mallory, Susan B., MD; "Diaper dermatitis," *Postgraduate Medicine*, vol. 98, No. 6, Dec., 1995, pp. 79–82, 84, 86.

Zielinski, Ruth, C.N.M., Hanson, Elizabeth, C.N.M.; "Diaper Dermatitis: Medical Aspects of Skin Care," *Nonwovens World*, Feb.–Mar., 2000, pp. 60–65.

Patent Abstracts of Japan 02043265 A: Description of Masaru et al. , "Thixotropic Semisolid Composition."

Patent Abstracts of Japan 02053709 A: Description of Masaru et al. , "Thixotropic Semi–Solid Composition."

Patent Abstracts of Japan 06065104 A: Description of Michio, "Powder Composition for Dermatic Application Prevented from Scatterability."

Patent Abstracts of Japan 07267839 A: Description of Yoshiko et al. , "Ointment Composition Adhesive to Oral Mucosa."

Patent Abstracts of Japan 09151112 A: Description of Yasuhiro et al. , "Microemulsion Composition,"

Patent Abstracts of Japan 10306039 A: Description of Christine et al. , "Solid Topical Aqueous Composition Capable of Forming Film, When Applied, and Having Gel Appearance."

Patent Abstracts of Japan 55025430 A: Description of Mikio et al. , "Thickening and Gelling Agent."

Patent Abstracts of Japan 56110611 A: Description of Mitsue et al. , "Preparation of Ointment Embrocation for Skin."

Patent Abstracts of Japan 59053409 A: Description of Susumu et al. , "Base Composition and Pharmaceutical Composition for External Use."

Patent Abstracts of Japan 59122420 A: Description of Katsuo et al. , "Local Ointment."

Patent Abstracts of Japan 59227816 A: Description of Kenji et al. , "Skin Cleaning and Wiping Agent Composition."

Patent Abstracts of Japan 60006759 A: Description of Tadashi et al. , "Water–Dispersible Resin for Cataplasm."

Patent Abstracts of Japan 61129117 A: Description of Sakahito et al. , "Aloe–Containing Cataplasm."

Patent Abstracts of Japan 61194014 A: Description of Hiroshi et al. , "Hydrophilic Base."

Patent Abstracts of Japan 63264413 A: Description of Kazuo, "Gabexate Mesylate Ointment."

American Society for Testing Materials (ASTM) Designation: D 1321–92, "Standard Test Method for Needle Penetration of Petroleum Waxes," pp. 483–485, published Dec. 1992.

American Society for Testing Materials (ASTM) Designation: D 3236–88, "Standard Test Method for Apparent Viscosity of Hot Melt Adhesives and Coating Materials," pp. 326–331, published Dec. 1988.

Federal Test Method Standard (FTMS) No. 191A, Method 5450, "Permeability To Air; Cloth; Calibrated Orifice Method," Jul. 20, 1978, 5 pages.

Federal Test Method Standard (FTMS) No. 191A, Method 5514, "Water Resistance of Cloth; Low Range, Hydrostatic Pressure Method," Jul. 20, 1978, 3 pages.

Barbero, G.J. et al., "Stool Trypsin and Chymotrysin," American Journal of Diseases of Children, vol. 112, Jul. through Dec., 1966, pp. 536–540.

Barry, B.W. and A.J. Grace, "Investigation of Semisolid Lipophilic Preparations by Small Strain and Continuous Shear Viscometry and Their Application to Texture Profile," Journal of Pharmaceutical Sciences, vol. 60, Jun. 1971, pp. 814–820.

Boylan, James C., "Rheological Study of Selected Pharmaceutical Semisolids," Journal of Pharmaceutical Sciences, vol. 55, No. 7, Jul. 1966, pp. 710–715.

Braudo, E.E. et al., "The Effect Produced by the Green Tea Components and Tannin on the Fermentative Activity of Trypsin in Vitro," Vopr Pitan, vol. 27, Issue No. 6, Nov.–Dec. 1968, pp. 40–44. (Russian w/English summary).

Bremecker, K.D. et al., "Novel Concept for a Mucosal Adhesive Ointment," Journal of Pharmaceutical Sciences, vol. 73, No. 4, Apr. 1984, pp. 548–552.

Davies, Owen L. and Peter L. Goldsmith, editors, Statistical Methods in Research and Production, Fourth Revised Edition, published by Longman Inc., New York, 1984, p. 460.

Davis, S.S. et al., "Some Limitations of Continous Shear Methods for the Study of Pharmaceutical Semi–Solids," Journal of Pharmacy and Pharmacology, vol. 20, Supplemental Issue, Dec. 1968, pp. 157S–167S.

Drechsler, Lee Ellen et al., "The Wipe: A Carrier of Skin Benefits," Cosmetics & Toiletries, vol. 116, No. 10, Oct. 2001, pp. 33–36, 38, 40, 42.

Eccleston, G.M. et al., "Correlation of Viscoelastic Functions for Pharmaceutical Semisolids: Comparison of Creep and Oscillatory Tests for Oil–in–Water Creams Stabilized by Mixed Emulsifers," Journal of Pharmaceutical Sciences, vol. 62, No. 12, Dec. 1972, 1954–1961.

Eccleston, G.M. "Structures and Rheology of Cetomacrogol Creams: The Influence of Alcohol Chain Length and Homologue Composition," Journal of Pharmacy and Pharmacology, vol. 29, No. 3, Mar. 1977, pp. 157–162.

Eros, I. and A. Thaleb, "Rheological Studies of Creams: I. Rheological Functions and Structure of Creams," Acta Pharmaceutica Hungarica, vol. 64, No. 3, May 1994, pp. 101–103.

Fuhrer, C., "Gel Structures of Fatty Alcohols in Ointment Bases," Pharmazie, vol. 26, No. 1, Jan. 1971, pp. 54–45. (German).

Haverback, Bernard J. et al., "Measurement of Trypsin and Chymotrypsin in Stool: A Diagnostic Test for Pancreatic Exocrine Insuffieciency," Gastroenterology, vol. 44, 1963, pp. 588–597.

Huttenrauch, R., "Activation Energies in Plastic Deformation of Ointment Gels," Pharmazie, vol. 28, No. 4, Apr. 1973, 244–249. (German).

Kedzierewicz, F. et al., "Preparation of Silicone Microshperes by Emulsion Polymerization: Application to the Encapsulation of a Hydrophilic Drug," Journal of Microencapsulation, vol. 15, No. 2, Mar.–Apr. 1998, pp. 227–236.

Muguet, V. et al. "Formulation of Shear Rate Sensitive Multiple Emulsions," Journal of Controlled Release, vol. 70, No. 1–2, Jan. 29, 2001, pp. 37–49.

Odio, Mauricio R. et al., "Continuous Topical Administration of a Petrolatum Formulation by a Novel Disposable Diaper. 1. Effect on Skin Surface Microtopography," Dermatology, 2000;200(3);232–237.

Odio, Mauricio R. et al., "Continuous Topical Administration of a Petrolatum Formulation by a Novel Disposable Diaper. 2. Effect on Skin Condition," Dermatology, 2000;200(3):238–243.

Pena, Lorraine E. et al., "Structural Rheology of a Model Ointment," Pharmaceutical Research, vol. 11, No. 6, Jun. 1994, pp. 875–881.

Popovici, Iuliana et al., "The Physico–Chemical Characterization and Therapeutic Evaluation of Cicatrol," Revista Medico–Chirurgicala Societatii Medici si Naturalisti din Lasi, vol. 96, No. 1–2, Jan.–Jun. 1992, pp. 57–64.

Salo, D.P. et al., "Ion Exchange Properties of Clay Minerals and Its Use for Obtaining Clays With Planned Properties. 3. Effect of the Nature of Exchange Kation on the Structure–Mechanical Properties of Suspensions and Ointments Bases Prepared From Clays of Montmorillonite and Sepiolite–Mountain Leather Groups," Farm Zh, vol. 23, No. 6, 1968, pp. 61–66. (Ukrainian).

Taleb, A. and I. Eros, "Rheological Studies of Creams. II. Effect of Water Content on Rheological Characteristics," Acta Pharmaceutica Hungarica, vol. 66, No. 2, Mar. 1996, pp. 71–76.

Tamburic, S. et al., "An Investigation Into the Use of Thermorheology and Texture Analysis in the Evaluation of W/O Creams Stabilized With a Silicone Emulsifier," Pharmaceutical Development Technology, vol. 1, No. 3, Oct. 1996, pp. 299–306.

Vinson, Joe and John Prouch, "Inhibition of Moisture Penetration to the Skin by a Novel Incontinence Barrier Product," Journal of Wound Ostomy Continence Nursing, vol. 25, No. 5, Sep. 1998, pp. 256–260.

American Society for Testing Materials (ASTM) Designation: D 1321—92, "Standard Test Method for Needle Penetration of Petroleum Waxes[1]", pp. 483–485, published Dec. 1992.

American Society for Testing Materials (ASTM) Designation: D 3236—88, "Standard Test Method for Apparent Viscosity of Hot Adhesives and Coating Materials[1]", pp. 326–331, published Dec. 1988.

Federal Test Method Standard No. 191A, Method 5514, "Water Resistance of Cloth; Low Range, Hydrostatic Pressure Method", Jul. 20, 1978.

Federal Test Method Standard No. 191A, Method 5450, "Permeability to Air; Cloth; Calibrated Orifice Method", Jul. 20, 1978.

Haverback, B. J., Dyce, B.J., Gutentag, P.J. and Montgomery, D. W. (1963) "Measurement of Trypsin and Chymotrypsin in Stool." *Gasteroenterology* 44:588–597.

Barbero, G.J., Sibings, M.S., Marino, J. M., and Seibel, R. (1966) "Stool Trypsin and Chymotrysin. "*Amer. J. Dis. Child* 112:536–540.

"Statistical Methods in Research and Production", p. 460, edited by Owen L. Davies and Peter L. Goldsmith, published by Longman Group Limited, fourth revised edition (1984).

* cited by examiner

HYDROPHILIC COMPOSITIONS FOR USE ON ABSORBENT ARTICLES TO ENHANCE SKIN BARRIER

FIELD OF THE INVENTION

The present invention relates to the inclusion of lipid-enriched, hydrophilic compositions with improved stability on the bodyfacing materials of disposable absorbent articles, such as diapers, training pants, adult incontinence products, underpants, feminine care products, nursing pads, wound dressings and similar articles having absorbent capacity. The present invention also relates to improving skin health by protecting and enhancing the barrier function of the skin through delivery of hydrophilic compositions from the bodyfacing materials of disposable absorbent articles to the skin. Prior to delivery to the skin, the compositions are stable on the bodyfacing materials. The compositions of the invention can also provide benefit to the barrier function of the skin when they are incorporated into other skin-contacting materials such as tissues, wet wipes and cosmetic cleansing or buffing pads.

BACKGROUND OF THE INVENTION

The stratum corneum is the outer-most layer of the skin and is responsible for regulating skin water levels and functioning as a barrier against chemicals and other stress agents found in the environment. The complex arrangement of lipids in the intercellular space of the stratum corneum is responsible for the establishment of normal barrier function. Multi-layered structures of cholesterol, ceramides and fatty acids, as well as some other minor lipids, provide the major barrier to the transport of substances into or through the skin. The overall structure of the stratum corneum acts as the frontline barrier to the skin. The link between skin barrier function and skin health is apparent from the skin inflammation caused by lipid extraction from the skin. That is, when skin barrier function is impaired, the other layers of the skin can be injured and have a response to that injury in the form of inflammation.

In the area of skin health, it is known to apply lipid-containing compositions to the skin in order to enhance the barrier function of the stratum corneum. This approach is disclosed in U.S. Pat. No. 5,643,899 issued to Elias et al. on Jul. 1, 1997. For some time, those of skill in the art have believed that it is necessary to apply all three of the lipid components of the stratum corneum (cholesterol, ceramides and fatty acids) to the skin in order to replenish and repair the skin and in order to not affect the normal repair processes of the skin. In particular, ceramides are believed to be very important. In fact, the art teaches that if fewer than all three of the components are used in a skin composition, the composition could actually compromise or delay repair of the barrier.

In U.S. patent application Ser. No. 09/382,018 now U.S. Pat. No. 6,475,197 filed Aug. 24, 1999, various compositions for improving skin health are described, including compositions suitable for use in conjunction with absorbent articles. The compositions in patent application Ser. No. 09/382,018 were found to provide benefits for skin health. The compositions were described as containing a variety of potential components and, in some forms, the compositions included natural fats and oils, sterols and sterol derivatives, humectants and surfactants. These compositions have been found to improve skin health even though they do not necessarily include any ceramides. Efficacy without ceramides was unexpected. Though the exact mechanism of functionality was not known, one hypothesis was that strongly hydrophilic components of the compositions, including hydrophilic solvent and high molecular weight polyethylene glycols, provided an overall composition that attracted water and that acted as a carrier to bring the lipid components into the skin. The surfactant and humectant components were believed to emulsify the lipid components into the composition. Further, these compositions included fatty alcohols that, together with the high molecular weight polyethylene glycols, were used to solidify the overall composition and to minimize the migration of the compositions into the nonwoven materials of the absorbent articles.

Therefore, benefits and improvements to skin health have been observed when compositions containing the lipids naturally present in the stratum corneum are applied to the skin. Though the exact mechanisms are not known, one hypothesis is that the lipids being applied with the compositions are replenishing lipids that have been lost from the stratum corneum as a result of physical or biological insults. Another hypothesis is that the lipids being applied with the compositions are providing additional lipids to the stratum corneum resulting in better protection against insults. The stratum corneum of the skin is constantly exposed to physical and biological insults that could have a negative effect on barrier function.

Absorbent articles such as diapers, training pants, incontinence products and feminine care products are worn such that they are in direct contact with the skin of the wearer. An unavoidable consequence of the use of absorbent articles is that the skin is exposed more directly to various physical and biological insults. Consequently, the barrier function of the skin covered by the absorbent article is put at risk. In order to provide disposability, absorbent articles are primarily constructed of nonwoven materials. Even though nonwoven materials are engineered to have soft hand and drape, they rub against the skin and there is friction. Such friction constitutes one form of physical insult to the skin barrier. Friction against the skin barrier also occurs with the use of absorbent tissues and wipes. Absorbent tissue and wipe products are frequently used for cleansing the skin areas covered by absorbent articles. Absorbent tissue and wipe products are necessary for removing biological waste materials from the skin.

In addition to these physical insults, skin covered by absorbent articles is also frequently exposed to biological insults. Biological fluids, such as urine, feces, vaginal secretions and nasal secretions, may contain a variety of components that can damage the skin barrier. Examples of these components include proteases, lipases and bile acids. Once the skin barrier is compromised, these components, in addition to other constituents of biological fluids, can initiate or exacerbate inflammation of the skin.

Diaper dermatitis is a genre of skin conditions that, in large part, originate from impaired skin barrier function. Impairment of the skin barrier can result from a variety of factors, including: increased skin hydration due to the occlusion of the skin caused by diapers, enzymatic skin damage due to fecal and urinary enzymes, and physical damage caused by friction against the diaper surface and repeated cleaning of the skin with absorbent tissues or wet wipes.

Excessive hydration of the skin also has a negative effect on the skin barrier. The hydration level of diapered skin, for example, may reach between five to ten times that of undiapered skin. Frequent contact of diapered skin with urine may also contribute to increased skin hydration.

Increased skin hydration disrupts skin lipid organization in the stratum corneum. This disruption may increase the permeability of the skin to irritants from feces and urine, thus increasing the risk of skin inflammation.

Disposable absorbent articles such as diapers, training pants, adult incontinence products, absorbent under pants, feminine care products and nursing pads have been used to absorb body fluids and leave the skin dry. Disposable absorbent articles of this type generally include a liquid impermeable backsheet member, an absorbent core or assembly, and a liquid permeable body facing or liner material. The body facing or liner material comes into contact with the wearer's skin. While the body facing material is made of a soft, compliant material, the material rubs against the skin during use and may not leave the skin completely dry and free of the bodily fluids, such as solid or semi-solid waste, the absorbent article is trying to absorb. During frequent insults of bodily fluids and frequent use of disposable absorbent articles, the skin can become irritated and appear red and be sore to the touch.

Creams, lotions or ointments can be used to provide an artificial hydrophobic barrier on the skin and to treat skin conditions such as diaper rash. Application of these types of products to the skin is often messy and inconvenient. Often, these products are not used prophylactically and are only used when signs of diaper rash are visible.

Diaper liners and other bodyfacing materials may be treated with emollients, such as petrolatum, that can be transferred to the skin through normal diapering practices. Once transferred to the skin, diaper liner formulations may provide an artificial barrier against feces and urine. These formulations may require high concentrations of petrolatum to ensure sufficient transfer to the skin to provide a benefit. High concentrations of petrolatum can be messy, greasy to the touch, and may impair the fluid handling properties of an absorbent article, such as a diaper. The slow penetration of petrolatum into the skin can lead to smearing of the agent over the skin and onto clothes and other materials.

Formulations, such as those containing petrolatum, are applied to the bodyfacing materials of absorbent articles during manufacture. In order to process and apply the formulations to the bodyfacing materials, the formulations need to be in a semi-solid or fluid state. However, in order to have stability on the bodyfacing material after manufacture, the formulations need to be semi-solid or solid across a wide range of shipping and storage temperatures. Not all of the presently known formulations are sufficiently stable on the bodyfacing materials. Consequently, such formulations may transfer off of the bodyfacing material prematurely or the formulations may migrate away from the skin-facing surfaces of the materials.

Thus, what is needed is a topically effective composition delivered from a bodyside or bodyfacing material of an absorbent article that protects, maintains, recovers or otherwise benefits skin barrier function against physical damage and irritants in biological fluids. It would also be desirable to provide a topical composition delivered from a bodyside material of an absorbent article that absorbs into the skin, is non-greasy and cosmetically acceptable to the consumer. Additionally, it would be desirable to provide a topical composition having improved stability on the bodyside material of an absorbent article. Further, it would be desirable to provide a topical composition delivered from a bodyside material of an absorbent article that does not impair the waste containment functions of the absorbent article.

SUMMARY OF THE INVENTION

In response to the difficulties and problems discussed above, compositions and the use of those compositions on absorbent articles for improving the barrier function of the skin have been discovered. The compositions of the invention provide several benefits associated with barrier function including protecting, strengthening, restoring and repairing the skin barrier. While the compositions of the inventions can have a variety of applications, the compositions are particularly beneficial when used in conjunction with absorbent articles such as diapers, incontinence garments, feminine care products, training pants, diaper pants, nursing pads and wound dressings. Additionally, the compositions of the invention could also provide benefits when used in conjunction with tissue, pre-moistened wipe products and cosmetic cleansing and buffing pads. A further benefit of the compositions of the invention is that the compositions show improved stability during processing and application to an article. The purposes and advantages of the present invention will be set forth in and apparent from the description that follows, as well as will be learned by practice of the invention. Additional advantages of the invention will be realized and attained by the compositions and articles particularly pointed out in the written description and claims hereof, as well as from the appended drawings.

In one aspect, the present invention relates to an absorbent article that includes an outer cover, a bodyside liner, an absorbent body and a composition. The bodyside liner is typically liquid permeable and defines a bodyfacing surface. The bodyside liner is connected in a generally superposed relation to the outer cover. The absorbent body is located between the bodyside liner and the outer cover. The composition is on a portion or the entire bodyfacing surface of the bodyside liner. The composition can be generally solid or semi-solid. The composition may be in a variety of forms, including, but not limited to, emulsions, lotions, creams, ointments, salves, suspensions, encapsulations, gels and the like. The composition can be applied to the bodyside liner using a variety of techniques including foam application, spraying, slot coating and printing. The present invention also encompasses technology that would permit integration of the composition directly with fibers or other materials used to form the bodyside liner. The compositions can be applied to the bodyfacing surface in amounts of from about 0.1 grams per meter squared ($g/m^2$) to about 30 $g/m^2$.

The compositions of the invention could also be applied to or be present on other skin contacting surfaces of absorbent articles such as the waist and leg elastics and the containment flaps. The compositions can include from about 10 to about 90 percent by weight of one or more hydrophilic solvents. More specifically, the compositions can include from about 25 to about 75 percent by weight of hydrophilic solvents. Desirably, the compositions of the invention can include from about 30 to about 60 percent by weight of hydrophilic solvents. Hydrophilic solvents include, but are not limited to, water, propylene glycol, low molecular weight polyethylene glycols (molecular weights of less than 720 daltons and liquid at room temperature), methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol solutions, hydrogenated starch hydrolysate, silicone glycols and mixtures of such compounds.

The compositions of the invention also include from about 5 to about 95 percent by weight of one or more high molecular weight polyethylene glycols having a molecular weight of at least about 720 daltons. More specifically, the compositions can include from about 10 to about 50 percent by weight of high molecular weight polyethylene glycols. Desirably, the compositions of the invention can include from about 15 to about 25 percent by weight of high molecular weight polyethylene glycols. The high molecular weight polyethylene glycols primarily function to provide the hydrophilic solvents and any active ingredients in solid form. In addition to providing a solid medium for the solvent, and reducing its tendency to migrate, the high molecular weight polyethylene glycols provide a tackiness to the hydrophilic composition that improves transfer to the skin of the wearer. As used herein, suitable high molecular weight polyethylene glycols include, but are not limited to, the following materials: polyethylene glycols having an average molecular weight of 720 daltons or greater, and the like, as well as mixtures thereof. These materials are not liquid at room temperature. Particularly suitable high molecular weight polyethylene glycols can have an average molecular weight of from 720 to about 1,840,000 daltons, more specifically from about 1400 to about 440,000 daltons, and still more specifically from about 1760 to about 10,570 daltons.

The compositions of the invention also include from about 1 to about 30 percent by weight of one or more fatty alcohols. More specifically, the compositions can include from bout 10 to about 25 percent by weight of fatty alcohols. Desirably, the compositions of the invention can include from about 15 to about 20 percent by weight of fatty alcohols. As used herein, suitable fatty alcohols include, but are not limited to, the following materials: alcohols having a carbon chain length of $C_{14}$–$C_{30}$ or greater, including cetyl alcohol, stearyl alcohol, arachidyl alcohol, behenyl alcohol, and mixtures thereof.

The compositions of the invention also include from about 1 to about 20 percent by weight of one or more emulsifying surfactants having an HLB range greater than 7 or a combination of low and high HLB surfactants that provide an HLB range greater than 7. More specifically, the compositions can include from about 2 to about 15 percent by weight of surfactants. Desirably, the compositions of the invention can include from about 3 to about 10 percent by weight of surfactants. Emulsifying surfactants are employed typically in cosmetic preparations to form emulsions of various components. The immiscible phase, such as an oil, is dispersed as droplets in the continuous phase, such as water or in this case the hydrophilic solvent. Suitable surfactants include, but are not limited to, Emulsifying Wax NF, Glyceryl Stearate, Glyceryl Stearate SE, Glycol Stearate, Glycol Stearate SE, Glycereth-20 Stearate, Glyceryl Behenate, Glyceryl Hydroxystearate, Glyceryl Laurate SE, Glyceryl Oleate, Glyceryl Oleate SE, Propylene Glycol Oleate, Propylene Glycol Oleate SE, Propylene Glycol Stearate, Propylene Glycol Stearate SE, Sorbitan Stearate, Sorbitan Trioleate, water dispersible metal soaps (Sodium Stearate), Behenyl Dimethicone Copolymers, Lauryl Methicone Copolymers, Cetyl Methicone Compolymers, Cetyl Dimethicone Copolymers, Stearyl Dimethicone Copolymers, Dimethicone Copolymers and mixtures there of.

The compositions of the invention also include from about 0.1 to about 30 weight percent of natural fats or natural oils. More specifically, the compositions can include from about 0.5 to about 20 percent by weight of natural fats or natural oils. Desirably, the compositions of the invention include from about 1 to about 10 percent by weight of natural fats, natural oils or mixtures of both. Natural fats and oils include fats, oils, essential oils, fatty acids, fatty alcohols, phospholipids and mixtures of these compounds. The natural fats and oils can be similar to the lipids that are present in healthy skin in order to mimic the naturally present lipids. Synthetic or synthetically modified fats and oils could potentially also be used if they functioned in the same manner as their natural counterparts. Examples of fats and oils include Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lanolin, Lanolin Alcohol, Lauric Acid, Palmitic Acid, Stearic Acid, Linoleic Acid, Stearyl Alcohol, Lauryl Alcohol, Myristyl Alcohol, Behenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil, PROLIPID 141 blend (available from International Specialty Products of Wayne, N.J.) and mixtures thereof.

The compositions of the invention also include sterols, sterol derivatives or mixtures of both in an amount of from about 0.1 to about 10 percent by weight. Sterols and sterol derivatives include compounds such as β-sterols with a tail on the 17 position and no polar groups, such as cholesterol, $C_{10}$–$C_{30}$ cholesterol/lanosterol esters, tall oil sterols, soy sterols, sterol esters and mixtures of these compounds. More specifically, the compositions include from about 0.5 to about 5 percent by weight of sterols, sterol derivatives or mixtures of both. Even more specifically, the compositions include from about 0.8 to about 3 percent by weight of the sterol compounds. Examples of suitable sterol compounds include cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyidecanoate, dihydrolanosterol, dihydrolanosteryl octyldecanoate, ergocalciferol, tall oil sterol, soy sterol acetate, lanasterol, soy sterol, avocado sterols, "AVOCADIN" (trade name of Croda, Ltd. in Parsippany, N.J.), sterol esters and mixtures thereof.

The compositions of the invention further include from about 0.1 to about 10 percent by weight of one or more emollients. More specifically, the compositions include from about 0.5 to about 5 percent by weight of emollient(s). Even more specifically, the compositions include from about 1 to about 5 percent by weight of emollient(s). Suitable emollients include petroleum based oils, petrolatum, vegetable oils, mineral oils, lanolin and its derivatives, fatty esters, glycerol esters and their derivatives, propylene glycol esters and their derivatives, alkoxylated carboxylic acids, alkyoxylated alcohols, fatty alcohols, alkyl methicones, alkyl dimethicones, phenyl silicones, alkyl trimethylsilanes, dimethicone and mixtures of such compounds.

The compositions of the invention can include the emollient and skin protectant, dimethicone. The dimethicone can be blended with the other components through the addition of water-based emulsions containing dimethicone such as emulsions having the trade designations "Dow Corning 1669 Emulsion" and "Dow Corning 1664 Emulsion" available from Dow Corning of Midland, Mich. The dimethicone can also be blended using a microencapsulated dimethicone such as are available from Lipo Technologies of Dayton, Ohio or from 3M of St. Paul, Minn. The dimethicone can also be added to the compositions of the invention in the form of an entrapped dimethicone. Dimethicone can be entrapped in "Polytrap" or "Microsponges" as are available from Advanced Polymer Systems of San Franciso, Calif. The dimethicone can also be incorporated in the form of a dimethicone treated powder such as dimethicone-treated talc or dimethicone-treated zinc oxide as are available from KOBO of South Plainfield, N.J.

Optionally, the compositions of the invention may include from about 1 percent by weight to about 20 percent by weight of one or more viscosity enhancers or rheology modifiers. The viscosity enhancers and rheology modifiers can be added to increase the melt point viscosity of the compositions. Increasing the melt point viscosity gives better stability of the compositions on the bodyfacing materials of the articles. The viscosity enhancers and rheology modifiers also improve the stability of the composition at the "hot box car" stability temperature of about 130° F. (54.5° C.). Suitable viscosity enhancers can include, but are not limited to, Actrylamides Copolymers, Agar, Gelatin, Water-Dispersable Metal Soaps, Butoxy Chitosan, Calcium Carboxymethyl Cellulose, Calcium Alginate, Carbomer, Carboxybutyl Chitosan, Carboxymethyl Chitosan, Carboxymethyl Dextran, Carboxymethyl Hydroxyethyl Cellulose, Cellulose Gum, DMAPA Acrylates/Acrylic Acid/Acrylonitrogens, Hectorite, Hydrated Silica, Hydroxyethyl Cellulose, Hydroxypropyl Guar, Hydroxypropyl Methylcellulose, Isobutylene/Sodium Maleate Copolymer, Kelp, Lithium Magnesium Silicate, Lithium Magnesium Sodium Silicate, Magnesium/Aluminum/Hydroxide/Carbonate, Magnesium Aluminum Silicate, Magnesium Silicate, Magnesium Trisilicate, Methoxy PEG-22/Dodecyl Glycol Copolymer, Metyl Cellulose, Metyl Hydroxyethylcellulose, Microcrystalline Cellulose, Montmorillonite, Nonoxynol Hydroxyethylcellulose, PEG Crosspolymer, Polyacrylate-3, Polyacrylic Acid, Polyethylene/isopropyl Maleate Copolymer, Polymethacrylic Acid, Polyvinyl Alcohol, PVP/Decene Copolymer, PVP Montmorillonite, Sodium Acrylates Copolymer, Sodium Acrylate/Vinyl Alcohol Copolymer, Sodium Acrylates/Vinyl Isodecanate Crosspolymer, Sodium Carboxymethyl Starch, Sodium Hydroxypropyl Starch Phosphate, Sodium Polyacrylate, TEA Alginate, TEA Carbomer, Xanthan Gum, Yeast Polysaccharides and mixtures thereof.

As will be described later in further detail, the compositions of the invention have been shown to enhance the barrier function of the stratum corneum of the skin. The presence of the compositions of the invention on the skin, when the skin is subjected to physical and biological insults, has been shown to be beneficial. Though the exact mechanism(s) is not known, it is possible that the compositions of the invention enhance the skin barrier because, upon transfer of the composition to the skin, the lipids (i.e., natural fats/oils, which contain non-essential and essential fatty acids, and the sterols) are readily available to penetrate into the stratum corneum and to help in the repair of the compromised natural barrier of the skin. If the natural barrier has not been compromised, the lipids provide a topical barrier to the penetration of harmful biological irritants found in feces, urine, menses and nasal discharge.

In addition to the components already described, the compositions of the invention may also include active ingredients such as those ingredients that may be useful for treating skin irritations such as diaper rash. Examples of such active ingredients include allantoin and its derivatives, aluminum hydroxide gel, calamine, cocoa butter, cod liver oil, dimethicone, kaolin and its derivatives, lanolin and its derivatives, mineral oil, petrolatum, shark liver oil, talc, topical starch, zinc acetate, zinc carbonate, zinc oxide and mixtures of these ingredients. Some of the ingredients listed as possible active ingredients for treating the skin can also be used as emollients.

In order to enhance or increase the function of the compositions of the invention, additional ingredients may be added. Examples of the classes of ingredients along with their functions include: antifoaming agents (reduce the tendency of foaming during processing); antimicrobial actives; antifungal actives; antiseptic actives; antioxidants (product integrity); antioxidants-cosmetic (reduce oxidation); astringents-cosmetic (induce a tightening or tingling sensation on skin); astringent-drug (a drug product that checks oozing, discharge or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth and pliable appearance of the skin by their ability to remain on the skin surface or in the stratum corneum to act as lubricants, to reduce flaking and to improve the skin's appearance); external analgesics (a topically applied drug that has a topical analgesic, anesthetic or antipruritic effect by depressing cutaneous sensory receptors, or that has a topical counterirritant effect by stimulating cutaneous sensory receptors); film formers (to hold active ingredients on the skin by producing a continuous film on skin upon drying); fragrances (consumer appeal); silicones/organomodified silicones (protection, tissue water resistance, lubricity, tissue softness); oils (mineral, vegetable and animal); natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents and suspending agents).

Ranges are used to describe the relative quantities of compounds in the compositions of the invention and ranges are used to describe the relative physical properties of the compositions of the invention. It is understood that the ranges are by way of illustration only and that one of skill in the art would recognize that the nature of the specific compositions dictates the levels to be applied to achieve the desired results. The levels of components are ascertainable by routine experimentation in view of the present disclosure.

The compositions of the invention typically have a melting point of from about 32° C. to about 100° C. Melting behavior in this range provides compositions that are relatively immobile and localized on the bodyfacing surface of the bodyside liner of the absorbent article at room temperature. Though relatively immobile and localized at room temperature, the compositions are also readily transferable to the wearer of the article at body temperature through natural rubbing or friction during wearing and through adhesion of the composition to the skin of the wearer. The compositions also maintain their integrity and are not completely liquid at elevated temperatures such as may be experienced during storage. Stability in a solid state at elevated temperatures is made possible, in part, by the melting point and rheology provided by the high molecular weight polyethylene glycol and the addition of viscosity enhancers/rheology modifiers, if needed, in the formulation. Desirably, the compositions of the invention are easily transferable to the skin by way of normal contact, including adhesion of the composition to the skin, wearer motion or body heat. Because the compositions are relatively immobilized on the bodyfacing surfaces of the articles, the quantities of the compositions necessary to provide the desired skin barrier benefits are reduced. In addition, special barrier or wrapping materials may not be necessary for the articles of the invention.

The compositions of the invention have viscosities that range from about 10 to about 10,000 centipoise as measured at a temperature of 60° C. At 55° C., the compositions have viscosities greater than about 200 centipoise. The compositions may also have a penetration hardness of from about 5 millimeters to about 365 millimeters at 25° C. The compositions can have process viscosities of less than about 100 centipoise under shear and pressure.

The present invention is further directed to a method of applying a composition to a bodyfacing surface of a bodyside liner of an absorbent article. The method of the invention includes a step of heating a composition to a temperature above the melting point of the composition. The composition can have a melting point of from about 32° C. to about 100° C. The composition can include one or more hydrophilic solvents, one or more high molecular weight polyethylene glycols having a molecular weight of at least 720 daltons, one or more $C_{14}$ to $C_{30}$ fatty alcohols, one or more emulsifying surfactants having a combined HLB in a range greater than 7, natural fats or oils, one or more sterols or sterol derivatives and one or more emollients. The composition can also include one or more viscosity enhancers or rheology modifiers. The method further includes a step of applying the composition to the bodyfacing surface of a bodyside liner of an absorbent article. The bodyfacing surface is that surface of the absorbent article that comes into contact with the skin of the wearer of the absorbent article. Other components of the absorbent article besides the bodyside liner may come into contact with the skin of the wearer. The composition can also be applied to those components including the waist elastics, the leg elastics, containment flaps and any other components coming into contact with the skin. The composition can be applied to the bodyfacing surface using a variety of techniques including foam application, spraying, slot coating, printing or combinations of these application techniques. The method of the invention also includes a step of resolidifying the composition. The composition can be resolidified in a variety of ways including chilling, slow cooling, curing or a combination of these techniques. After resolidification, the composition typically has a static viscosity of greater than about 200 centipoise. Further, the composition can have a penetration hardness of from about 5 to about 365 millimeters at 25° C. after the step of resolidification.

In another embodiment, the present invention is directed to a composition. While the composition may have other useful functions, the composition generally provides a benefit to the function of the skin barrier. The composition can include from about 10 to about 90 percent by weight of one or more hydrophilic solvents, or a mixture of hydrophilic solvents. The composition can also include from about 5 to about 95 percent by weight of one or more high molecular weight polyethylene glycols having a molecular weight of at least 720 daltons, or mixtures of such glycols. The composition further includes from about 1 to about 30 percent by weight of one or more $C_{14}$ to $C_{30}$ fatty alcohols, or a mixture of such fatty alcohols. The composition can also include from about 1 to about 20 percent by weight of one or more emulsifying surfactants, including oil-in-water surfactants, having a combined HLB with a range greater than 7, or mixtures of such surfactants. The composition can include from about 0.1 to about 30 percent by weight of one or more natural fats or oils, or the composition can include a mixture of one or more natural fats and oils. The composition can also include from about 0.1 to about 10 percent by weight of one or more sterols, sterol derivatives or mixtures of both sterols and sterol derivatives. An additional component of the composition of the invention can be from about 10 to about 10 percent by weight of one or more emollients. The composition can further include from about 1 to about 20 percent by weight of one or more viscosity enhancers or rheology modifiers.

The composition of the invention can have a melting point of from about 32° C. to about 100° C. depending on the function for which the composition is intended to be employed. If the composition is intended to be applied to an absorbent article, it may be desirable for the composition to have a melting point such that the composition is immobile at room temperature. Depending on the processing and handling to which the composition will be exposed, it may be beneficial for the composition to have a process viscosity of less than about 100 centipoise under shear and pressure. The composition can have a penetration hardness of from about 5 to about 365 millimeters at 25° C. Examples of specific compounds for the hydrophilic solvent, high molecular weight polyethylene glycol, fatty alcohol, oil-in-water emulsifying surfactant/surfactant combination, fat/oil, sterol/sterol derivative, emollient and viscosity enhancer/rheology modifier components of the composition can be as described previously and as will be described herein.

In an additional embodiment, the present invention is directed to a method for improving skin barrier function of a skin surface of a user. The method can include a step of contacting the skin surface of a user with a bodyfacing surface of a liner material. The liner material may be any type of woven or non-woven material. More specifically, the liner material is of a material that is typically used for the bodyside liner of an absorbent article. The bodyfacing surface has a composition on it. The composition can include a hydrophilic solvent, a high molecular weight polyethylene glycol having a molecular weight of at least 720 daltons, a $C_{14}$ to $C_{30}$ fatty alcohol, an oil-in-water emulsifying surfactant having a combined HLB in a range greater than 7, natural fat or oil, a sterol or sterol derivative, an emollient and a viscosity enhancer/rheology modifier. More specifically, the composition can include from about 10 to about 90 percent by weight of hydrophilic solvent, from about 5 to about 95 percent by weight of high molecular weight polyethylene glycol, from about 1 to about 30 percent by weight of $C_{14}$ to $C_{30}$ fatty alcohol, from about 1 to about 20 percent by weight of oil-in-water emulsifying surfactant/surfactant combination, from about 0.1 to about 30 percent by weight of natural fats or oils, from about 0.1 to about 10 percent by weight of sterols or sterol derivatives, from about 0.1 to about 10 percent by weight of emollients and, optionally, from about 1 to about 20 percent by weight of viscosity enhancers/rheology modifiers.

The method can also include a step of maintaining the bodyfacing surface of the liner material in contact with the skin surface of a user for a sufficient amount of time to transfer the composition to the skin surface. For purposes of the method, a sufficient amount of time would be the amount of time necessary for enough of the composition to have been transferred so as to enhance the skin barrier. The method of the invention further includes a step of repeating contact of the skin surface with the bodyfacing surface of the liner material for a sufficient amount of time in order to have an improvement in the skin barrier function of the wearer's skin. The repeated contact can occur by either applying additional composition to the bodyfacing surface of the liner material or by applying a new liner material having a full amount of the composition on the bodyfacing surface.

The absorbent articles, methods and compositions of the invention advantageously enhance the skin barrier in such a way not observed with conventional absorbent articles and compositions. Consequently, use of the absorbent articles and compositions of the invention enhance the skin barrier to protect against damage caused by physical and biological irritations. It is to be understood that both the foregoing general description and the following detailed description are exemplary and are intended to provide further explanation of the invention claimed. The accompanying drawings, that are incorporated in and constitute part of this specification, are included to illustrate and provide a further understanding of the articles, methods and compositions of the invention. Together with the description, the drawings serve to explain the various aspects of the invention.

BRIEF DESCRIPTION OF THE DRAWINGS

The present invention will be more fully understood and further advantages will become apparent when reference is made to the following detailed description of the invention and the accompanying drawings. The drawings are merely representative and are not intended to limit the scope of the claims. Like parts of the absorbent articles depicted in the drawings are referred to by the same reference numerals.

DETAILED DESCRIPTION OF THE INVENTION

The present invention is directed to solving problems related to enhancing the barrier function of the skin when the skin is exposed to causes of physical and biological damage. Similarly, the present invention is directed to solving problems related to the prevention and treatment of diaper rash.

The present invention encompasses compositions, compositions as they are applied to the bodyfacing materials of absorbent articles, absorbent articles including compositions and methods of applying compositions to absorbent articles. The following detailed description will be made in the context of one type of absorbent article, a disposable diaper that is adapted to be worn by infants about their lower torso. It is readily apparent, however, that the absorbent article of the present invention would also be suitable for use as another type of absorbent article, such as a feminine care pad, an incontinence garment, a training pant, a prefastened or refastenable diaper pant, a wound dressing or a nursing pad. Further, the compositions of the invention are not limited to application on the bodyfacing materials of absorbent articles. For example, the compositions of the inventions could be used on skin-contacting substrates such as tissues, wet (pre-moistened) wipe materials and cosmetic pads (such as for cleansing or buffing).

Figure 1:
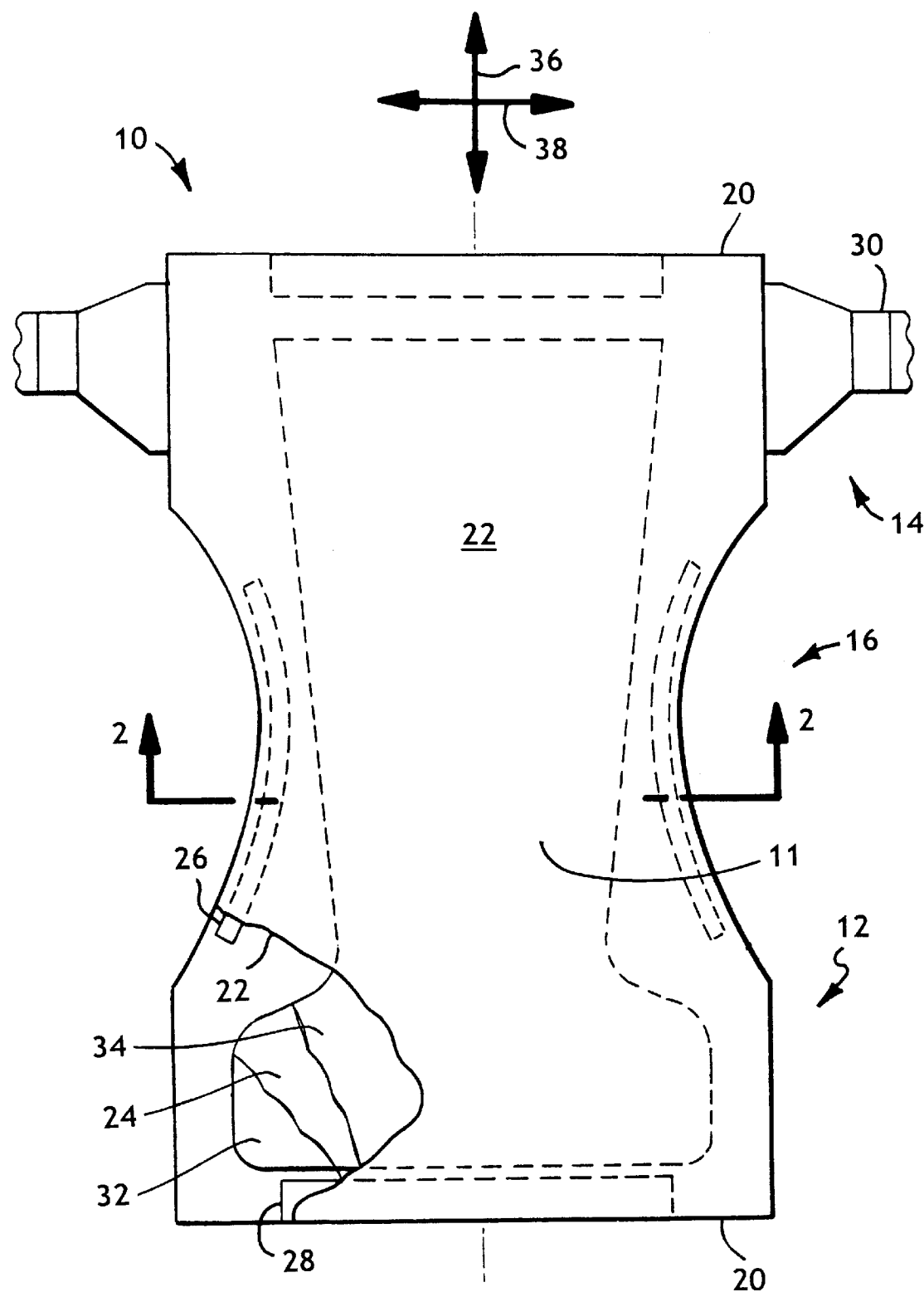
FIG. 1 representatively shows a partially cut away, top plan view of an absorbent article according to one embodiment of the invention in a stretched and laid flat condition with the surface of the article that contacts the skin of the wearer facing the view.

FIG. 1 is a representative plan view of a disposable diaper 10 of the present invention in a flat-out, uncontracted state (i.e., with all elastic induced gathering and contraction removed). The bodyfacing surface 11 of the diaper 10, that is, the surface 11 of the diaper 10 that contacts the wearer is facing the viewer. The compositions of the invention can be applied to one or more bodyfacing materials that are components of the diaper 10. As used herein, the term 'bodyfacing material' includes, but is not limited to, materials such as the bodyside liner or topsheet, elastic material, tissue, intake and distribution material, absorbent material, and backsheet material. Each of these materials and components of a diaper 10 are described more fully herein. The compositions of the invention are applied to one or more of the bodyfacing materials in order to have a beneficial effect on the skin barrier. The bodyfacing material of the present invention can be a single layer or multi-layered.

With reference to FIG. 1, the diaper 10 generally defines a front waist section 12, a rear waist section 14, and an intermediate section 16 that interconnects the front and rear waist sections 12 and 14. The front and rear waist sections 12 and 14 include the general portions of the diaper 10 that are constructed to extend substantially over the wearer's front and rear abdominal regions, respectively, during use. The intermediate section 16 of the diaper 10 includes the general portion of the diaper 10 that is constructed to extend through the wearer's crotch region between the legs.

The diaper 10 includes a vapor permeable backsheet or outer cover 20, a liquid permeable topsheet or bodyside liner 22 positioned in facing relation with the outer cover 20, and an absorbent body 24, such as an absorbent pad, which is located between the outer cover 20 and the bodyside liner 22. The outer cover 20 defines a length and a width that, in the illustrated embodiment, coincide with the length and width of the diaper 10. The absorbent body 24 generally defines a length and width that are less than the length and width of the outer cover 20, respectively. Thus, marginal portions of the diaper 10, such as marginal sections of the outer cover 20, may extend past the terminal edges of the absorbent body 24. In the illustrated embodiments, for example, the outer cover 20 extends outwardly beyond the terminal marginal edges of the absorbent body 24 to form side margins and end margins of the diaper 10. The bodyside liner 22 is generally coextensive with the outer cover 20 but may optionally cover an area that is larger or smaller than the area of the outer cover 20, as desired. In other words, the bodyside liner 22 is connected in superposed relation to the outer cover 20. The outer cover 20 and bodyside liner 22 are intended to face the garment and body of the wearer, respectively, while in use.

To provide improved fit and to help reduce leakage of body exudates from the diaper 10, the diaper side margins and end margins may be elasticized with suitable elastic members, such as single or multiple strands of elastic. The elastic strands may be composed of natural or synthetic rubber and may optionally be heat shrinkable or heat elasticizable. For example, as representatively illustrated in FIG. 1, the diaper 10 may include leg elastics 26 which are constructed to operably gather and shirr the side margins of the diaper 10 to provide elasticized leg bands which can closely fit around the legs of the wearer to reduce leakage and provide improved comfort and appearance. Similarly, waist elastics 28 can be employed to elasticize the end margins of the diaper 10 to provide elasticized waists. The waist elastics 28 are configured to operably gather and shirr the waist sections to provide a resilient, comfortably close fit around the waist of the wearer. In the illustrated embodiments, the elastic members are illustrated in their uncontracted, stretched condition for the purpose of clarity.

Fastening means, such as hook and loop fasteners 30, are employed to secure the diaper 10 on a wearer. Alternatively, other fastening means, such as buttons, pins, snaps, adhesive tape fasteners, cohesives, mushroom-and-loop fasteners, or the like, may be employed. Additionally, more than two fasteners can be provided, particularly if the diaper 10 is to be provided in a prefastened configuration. The fasteners can vary in size and form.

The diaper 10 may further include other layers between the absorbent body 24 and the bodyside liner 22 or outer cover 20. For example, as representatively illustrated in FIGS. 1 and 2, the diaper 10 may include a ventilation layer 32 located between the absorbent body 24 and the outer cover 20 to insulate the outer cover 20 from the absorbent body 24, to improve air circulation and to effectively reduce the dampness of the garment facing surface of the outer cover 20. The ventilation layer 32 may also assist in distributing fluid exudates to portions of the absorbent body 24 that do not directly receive the insult. The diaper 10 may also include a surge management layer 34 located between the bodyside liner 22 and the absorbent body 24 to prevent pooling of the fluid exudates and further improve air exchange and distribution of the fluid exudates within the diaper 10.

The diaper 10 may be of various suitable shapes. For example, the diaper may have an overall rectangular shape, T-shape or an approximately hourglass shape. In the shown embodiment, the diaper 10 has a generally I-shape. The diaper 10 further defines a longitudinal direction 36 and a lateral direction 38. Other suitable diaper components that may be incorporated on absorbent articles of the present invention include containment flaps, waist flaps, elastomeric side panels, and the like which are generally known to those skilled in the art. Likewise, if the diaper 10 is to be sold in a prefastened condition, the diaper 10 may have passive bonds (not shown) that join the rear waist section 14 with the front waist section 12.

Examples of diaper configurations suitable for use in connection with the instant application that may include other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5, 1993, to Bruemmer et al.; U.S. Pat. No. 5,192,606 issued Mar. 9, 1993, to Proxmire et al., and U.S. Pat. No. 5,509,915 issued Apr. 23, 1996 to Hanson et al., the disclosures of which are herein incorporated by reference.

The various components of the diaper 10 are integrally assembled together employing various types of suitable attachment means, such as adhesive, sonic bonds, thermal bonds or combinations thereof. In the shown embodiment, for example, the bodyside liner 22 and outer cover 20 are assembled to each other and to the absorbent body 24 with lines of adhesive, such as a hot melt, pressure-sensitive adhesive. Similarly, other diaper components, such as the elastic members 26 and 28, fastening members 30, and ventilation and surge layers 32 and 34 may be assembled into the diaper 10 by employing the above-identified attachment mechanisms.

The outer cover 20 of the diaper 10, as representatively illustrated in FIG. 1, is composed of a substantially vapor permeable material. The permeability of the outer cover 20 is configured to enhance the breathability of the diaper 10 and to reduce the hydration of the wearer's skin during use without allowing excessive condensation of vapor, such as urine, on the garment facing surface of the outer cover 20 that can undesirably dampen the wearer's clothes. The outer cover 20 is generally constructed to be permeable to at least water vapor and has a water vapor transmission rate of at least about 1000 $g/m^2/24$ hr., desirably at least about 1500 $g/m^2/24$ hr, more desirably at least about 2000 $g/m^2/24$ hr., and even more desirably at least about 3000 $g/m^2/24$ hr. For example, the outer cover 20 may define a water vapor transmission rate of from about 1000 to about 6000 $g/m^2/24$ hr. Materials that have a water vapor transmission rate less than those above do not allow a sufficient amount of air exchange and undesirably result in increased levels of skin hydration.

The outer cover 20 is also desirably substantially liquid impermeable. For example, the outer cover 20 may be constructed to provide a hydrohead value of at least about 60 cm, desirably at least about 80 cm, and more desirably at least about 100 cm when subjected to the Hydrostatic Pressure Test. Materials that have hydrohead values less than those above undesirably result in the strike through of liquids, such as urine, during use. Such fluid strike through can undesirably result in a damp, clammy feeling on the outer cover 20 during use.

The outer cover 20 may be composed of any suitable materials that either directly provide the above desired levels of liquid impermeability and air permeability or, in the alternative, materials that can be modified or treated in some manner to provide such levels. In one embodiment, the outer cover 20 may be a nonwoven fibrous web constructed to provide the required level of liquid impermeability. For example, a nonwoven web composed of spunbond or meltblown polymer fibers may be selectively treated with a water repellent coating or laminated with a liquid impermeable, vapor permeable polymer film to provide the outer cover 20. In a particular embodiment of the invention, the outer cover 20 may include a nonwoven web composed of a plurality of randomly deposited hydrophobic thermoplastic meltblown fibers that are sufficiently bonded or otherwise connected to one another to provide a substantially vapor permeable and substantially liquid impermeable web. The outer cover 20 may also include a vapor permeable nonwoven layer that has been partially coated or otherwise configured to provide liquid impermeability in selected areas.

Examples of suitable materials for the outer cover 20 are also described in U.S. Pat. No. 5,482,765 issued Jan. 9, 1996 in the name of Bradley et al. and entitled "NONWOVEN FABRIC LAMINATE WITH ENHANCED BARRIER PROPERTIES"; U.S. Pat. No. 5,879,341 issued Mar. 9, 1999 in the name of Odorzynski et al. and entitled "ABSORBENT ARTICLE HAVING A BREATHABILITY GRADIENT"; U.S. Pat. No. 5,843,056 issued Dec. 1, 1998, in the name of Good et al. and entitled "ABSORBENT ARTICLE HAVING A COMPOSITE BREATHABLE BACKSHEET"; and U.S. patent application Ser. No. 08/882,712 filed Jun. 25, 1997 now U.S. Pat. No. 6,309,736, in the name of McCormack et al. and entitled "LOW GAUGE FILMS AND FILM/NONWOVEN LAMINATES", the disclosures of which are herein incorporated by reference.

In a particular embodiment, the outer cover 20 is provided by a microporous film/nonwoven laminate material that includes a spunbond nonwoven material laminated to a microporous film. The spunbond nonwoven comprises filaments of about 1.8 denier extruded from a copolymer of ethylene with about 3.5 weight percent propylene and defines a basis weight of from about 17 to about 25 grams per square meter. The film comprises a cast coextruded film having calcium carbonate particles therein and defines a basis weight of about 58 grams per square meter prior to stretching. The film is preheated, stretched and annealed to form the micropores and then laminated to the spunbond nonwoven. The resulting microporous film/nonwoven laminate based material has a basis weight of from about 30 to about 60 grams per square meter and a water vapor transmission rate of from about 3000 to about 6000 $g/m^2/24$ hr. Examples of such film/nonwoven laminate materials are described in more detail in U.S. patent application Ser. No. 08/882,712 filed Jun. 25, 1997, in the name of McCormack et al. and entitled "LOW GAUGE FILMS AND FILM/NONWOVEN LAMINATES", the disclosure of which has been incorporated by reference.

In another embodiment, the outer cover 20 is provided by an extensible material. Further, the outer cover 20 can also be provided by a material having stretch in both the longitudinal 36 and lateral 38 directions. When the outer cover 20 is made from extensible or stretchable materials, the diaper 10 provides additional benefits to the wearer including improved fit.

Figure 2:
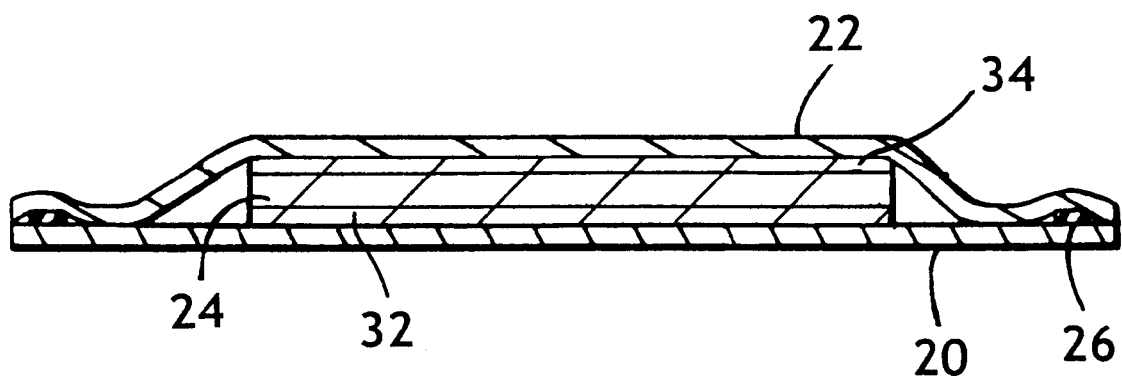
FIG. 2 representatively shows a sectional view of the absorbent article of FIG. 1 taken along line 2—2.

The bodyside liner 22, as representatively illustrated in FIGS. 1 and 2, defines a bodyfacing surface 11 that is compliant, soft feeling, and nonirritating to the wearer's skin. Further, the bodyside liner 22 may be less hydrophilic than the absorbent body 24, to present a relatively dry surface to the wearer, and may be sufficiently porous to be liquid permeable, permitting liquid to readily penetrate through its thickness. A suitable bodyside liner 22 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 22 is suitably employed to help isolate the wearer's skin from liquids held in the absorbent body 24.

Various woven and nonwoven fabrics can be used for the bodyside liner 22. For example, the bodyside liner 22 may be composed of a meltblown or spunbond web of polyolefin fibers. The bodyside liner 22 may also be a bonded-carded web composed of natural and/or synthetic fibers. The bodyside liner 22 may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 22 comprises a nonwoven, spunbond, polypropylene fabric composed of about 2.8–3.2 denier fibers formed into a web having a basis weight of about 22 grams per square meter and a density of about 0.06 gram per cubic centimeter.

In a particular embodiment of the present invention, the bodyside liner 22 may be surface treated with about 0.3 weight percent of a surfactant mixture that contains a mixture of AHCOVEL Base N-62 surfactant and GLUCOPON 220UP surfactant in about a 3:1 ratio based on a total weight of the surfactant mixture. The AHCOVEL Base N-62 surfactant is purchased from Hodgson Textile Chemicals Inc., a business having offices in Mount Holly, N.C., and includes a blend of hydrogenated ethoxylated castor oil and sorbitan monooleate in a 55:45 weight ratio. The GLUCOPON 220UP surfactant is purchased from Henkel Corporation and includes alkyl polyglycoside. The surfactant may also include additional ingredients such as aloe. The surfactant may be applied by any conventional means, such as spraying, printing, brush coating, foam or the like. The surfactant may be applied to the entire bodyside liner 22 or may be selectively applied to particular sections of the bodyside liner 22, such as the medial section along the longitudinal centerline of the diaper, to provide greater wettability of such sections.

The absorbent body 24 of the diaper 10, as representatively illustrated in FIG. 1, may suitably comprise a matrix of hydrophilic fibers, such as a web of cellulosic fluff, mixed with particles of a high-absorbency material commonly known as superabsorbent material. In a particular embodiment, the absorbent body 24 includes a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. Alternatively, the absorbent body 24 may include a laminate of fibrous webs and superabsorbent material or other suitable matrix for maintaining a superabsorbent material in a localized area.

The absorbent body 24 may have any of a number of shapes. For example, the absorbent body 24 may be rectangular, I-shaped, or T-shaped. It is generally preferred that the absorbent body 24 is narrower in the intermediate section than in the front or rear waist sections of the diaper 10. The absorbent body 24 may be provided by a single layer or, in the alternative, may be provided by multiple layers, all of which need not extend the entire length and width of the absorbent body 24. In a particular aspect of the invention, the absorbent body 24 can be generally T-shaped with the laterally extending cross-bar of the "T" generally corresponding to the front waist section 12 of the absorbent article for improved performance, especially for male infants. In the illustrated embodiments, for example, the absorbent body 24 across the front waist section 12 of the article has a cross-directional width of about 18 centimeters, the narrowest portion of the intermediate section 16 has a width of about 7.5 centimeters and in the rear waist section 14 has a width of about 11.4 centimeters.

The size and the absorbent capacity of absorbent body 24 should be compatible with the size of the intended wearer and the liquid loading imparted by the intended use of the absorbent article. Further, the size and the absorbent capacity of the absorbent body 24 can be varied to accommodate wearers ranging from infants through adults. In addition, it has been found that with the present invention, the densities and/or basis weights of the absorbent body 24 can be varied. In a particular aspect of the invention, the absorbent body 24 has an absorbent capacity of at least about 300 grams of synthetic urine.

In embodiments wherein the absorbent body 24 includes the combination of hydrophilic fibers and high-absorbency particles, the hydrophilic fibers and high-absorbency particles can form an average basis weight for the absorbent body 24 that is within the range of about 400–900 grams per square meter. In certain aspects of the invention, the average composite basis weight of such an absorbent body 24 is within the range of about 500–800 grams per square meter, and preferably is within the range of about 550–750 grams per square meter to provide the desired performance.

To provide the desired thinness dimension to the various configurations of the absorbent article of the invention, the absorbent body 24 can be configured with a bulk thickness that is not more than about 0.6 centimeters. Preferably, the bulk thickness is not more than about 0.53 centimeters, and more preferably is not more than about 0.5 centimeters to provide improved benefits. The bulk thickness is determined under a restraining pressure of 0.2 psi (1.38 kPa).

The high-absorbency material can be selected from natural, synthetic, and modified natural polymers and materials. The high-absorbency materials can be inorganic materials, such as silica gels, or organic compounds, such as crosslinked polymers. The term "crosslinked" refers to methods for effectively rendering normally water-soluble materials substantially water insoluble but swellable. Such methods include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrrolidone), poly(vinyl morpholinone), poly(vinyl alcohol), and mixtures and copolymers thereof. Further polymers suitable for use in the absorbent body 24 include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthan gum, locust bean gum, and the like. Mixtures of natural and wholly or partially synthetic absorbent polymers can also be useful in the present invention.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. In general, the high absorbency material is present in the absorbent body 24 in an amount of from about 5 to about 90 percent by weight, desirably in an amount of at least about 30 percent by weight, and even more desirably in an amount of at least about 50 percent by weight based on a total weight of the absorbent body 24. For example, in a particular embodiment, the absorbent body 24 may include a laminate which includes at least about 50 percent by weight and desirably at least about 70 percent by weight of high-absorbency material overwrapped by a fibrous web or other suitable material for maintaining the high-absorbency material in a localized area.

An example of high-absorbency material suitable for use in the present invention is SANWET IM 3900 polymer available from Hoechst Celanese, a business having offices in Portsmouth, Va. Other suitable superabsorbents may include FAVOR SXM 880 polymer obtained from Stockhausen, a business having offices in Greensboro, N.C.

Optionally, a substantially hydrophilic tissue wrapsheet (not illustrated) may be employed to help maintain the integrity of the structure of the absorbent body 24. The tissue wrapsheet is typically placed about the absorbent body 24 over at least the two major facing surfaces thereof. The tissue wrapsheet can be composed of an absorbent cellulosic material, such as creped wadding or a high wet-strength tissue. In one aspect of the invention, the tissue wrapsheet can be configured to provide a wicking layer that helps to rapidly distribute liquid over the mass of absorbent fibers constituting the absorbent body 24.

The absorbent body 24 of the different aspects of the present invention further includes a plurality of zones of high air permeability which allow air and vapors to readily pass through the absorbent body 24 and through the vapor permeable outer cover 20 out of the diaper 10 into ambient air. For example, the absorbent body 24 may include a plurality of air passageways that provide the absorbent body 24 with zones or regions of high air permeability. The portions of the absorbent body 24 adjacent the air passageways provide zones or regions of high absorption. The zones of high air permeability are designed to provide the maximum air exchange from the absorbent body 24 while the zones of high absorption are designed to receive and hold the majority of the body exudates. The absorbent body 24 may define any number of zones of high air permeability that provide the improved air exchange. Desirably, the absorbent body 24 defines at least 3 and more desirably at least 5 different zones of high air permeability for improved performance.

The zones of high air permeability, such as the air passageways, are configured to enhance the breathability of the article to reduce the hydration of the wearer's skin during use without allowing excessive condensation of vapor, such as urine, on the garment facing surface of the outer cover 20. Such condensation of vapor on the outer surface of the diaper 10 can undesirably dampen the wearer's clothes. The zones of high air permeability are generally located in the area of the diaper over which air and vapor can transfer from the bodyside liner 22, through the absorbent body 24 and any other intervening layer or layers of material, and out the vapor permeable outer cover 20. For example, the zones of high air permeability may be located throughout the entire absorbent body 24 or may be selectively located in those regions of the absorbent body 24 that provide the maximum air exchange, such as the intermediate section 16 of the diaper 20. In a particular embodiment, the zones of high air permeability are located in the front and intermediate sections 12 and 16, respectively, of the diaper 10 for improved air exchange.

The zones of high absorption, on the other hand, are not designed to transfer a high level of air and vapor from the interior of the diaper 10. Thus, the air exchange from the bodyside liner 22 of the diaper 10 to the outer cover 20 of the diaper and into the ambient atmosphere (exterior of the diaper 10) occurs generally through the absorbent body 24 in the zones of high air permeability. Some air exchange through the absorbent body 24 can also occur in the zones of high absorption to a limited degree. The zones of high air permeability may have any desired configuration including rectangular, circular, hourglass, oval, and the like, and may also include selected longitudinal or lateral strips or multiple regions which may be intermittently located.

The zones of high air permeability may have any desired dimensions that effectively provide improved air exchange while preventing excessive condensation of vapor from the absorbent body 24 through and onto the garment facing surface of the outer cover 20. Desirably, the zones of high air permeability may define a total area of from about 5 to about 75 percent, more desirably at least about 10 percent, even more desirably from about 10 to about 70 percent, and still more desirably from about 10 to about 60 percent of the total surface area of the absorbent body 24 of the diaper 10. For example, in a diaper 10 intended for use on a medium sized infant, the zones of high air permeability may define a total area of from about 6 to about 90 square centimeters.

When the total area of the zones of high air permeability is greater than the above amounts, the diaper 10 may exhibit an undesirable amount of condensation of vapor on the exposed, garment facing surface of the outer cover 20 undesirably resulting in a clammy feeling on the outer surface of the diaper 10. Whereas, when the total area of the zones of high air permeability is less than the above amounts, the diaper 10 may exhibit a low level of air exchange resulting in high levels of skin hydration that can undesirably lead to skin irritation and rash.

The zones of high air permeability of the absorbent body 24 of the diaper 10 are constructed to be substantially permeable to at least air and preferably permeable to water vapor. For example, the zones of high air permeability of the absorbent body 24 define a Frazier Porosity value which is at least about 10 percent, more desirably at least about 20 percent and even more desirably at least about 50 percent greater than the Frazier Porosity value of the zones of high absorption of the absorbent body 24. As used herein, the term "Frazier Porosity" refers to the value determined according to the Frazier Porosity Test set forth below. When the zones of high air permeability exhibit Frazier Porosity values less than those indicated above, the diaper 10 may exhibit a low level of air exchange resulting in high levels of skin hydration that can undesirably lead to skin irritation and rash.

The zones of high air permeability may be provided in a variety of ways. The zones of high air permeability may be integral portions of the absorbent body 24 of the absorbent article or may be provided by apertures, holes or open spaces in the absorbent body 24. For example, portions of the absorbent body 24 may be discontinuous or removed to provide the zones. Alternatively, the zones of high air permeability may be provided by portions of the absorbent body 24 that are constructed to absorb less fluid exudates thereby resulting in improved air flow through such portions in use. For example, portions of the absorbent body 24 may be void of or contain substantially less high-absorbency material than other portions of the absorbent body 24 to provide such improved air flow. Portions of the absorbent body 24 may otherwise be treated or coated with a solution that renders them hydrophobic to provide the zones of high air permeability in selected areas. In other alternative configurations, the zones of high air permeability may be provided by creating voids or holes in the absorbent body 24 and placing other materials having a higher air permeability than the absorbent body 24, such as those materials described below as being suitable for the surge management layer 34, in the holes or voids.

Due to the thinness of absorbent body 24 and the high absorbency material within the absorbent body 24, the liquid uptake rates of the absorbent body 24, by itself, may be too low, or may not be adequately sustained over multiple insults of liquid into the absorbent body 24. To improve the overall liquid uptake and air exchange, the diaper 10 of the different aspects of the present invention may further include a porous, liquid-permeable layer of surge management material 34, as representatively illustrated in FIG. 1. The surge management layer 34 is typically less hydrophilic than the absorbent body 24, and has an operable level of density and basis weight to quickly collect and temporarily hold liquid surges, to transport the liquid from its initial entrance point and to substantially completely release the liquid to other parts of the absorbent body 24. This configuration can help prevent the liquid from pooling and collecting on the portion of the diaper 10 positioned against the wearer's skin, thereby reducing the feeling of wetness by the wearer. The structure of the surge management layer 34 also generally enhances the air exchange within the diaper 10.

Various woven and nonwoven fabrics can be used to construct the surge management layer 34. For example, the surge management layer 34 may be a layer composed of a meltblown or spunbond web of synthetic fibers, such as polyolefin fibers. The surge management layer 34 may also be a bonded-carded-web or an airlaid web composed of natural and synthetic fibers. The bonded-carded-web may, for example, be a thermally bonded web that is bonded using low melt binder fibers, powder or adhesive. The webs can optionally include a mixture of different fibers. The surge management layer 34 may be composed of a substantially hydrophobic material, and the hydrophobic material may optionally be treated with a surfactant or otherwise processed to impart a desired level of wettability and hydrophilicity. In a particular embodiment, the surge management layer 34 includes a hydrophobic, nonwoven material having a basis weight of from about 30 to about 120 grams per square meter.

For example, in a particular embodiment, the surge management layer 34 may include a bonded-carded-web, nonwoven fabric that includes bicomponent fibers and that defines an overall basis weight of about 83 grams per square meter. The surge management layer 34 in such a configuration can be a homogeneous blend composed of about 60 weight percent polyethylene/polyester (PE/PET), sheath-core bicomponent fibers that have a fiber denier of about 3 d and about 40 weight percent single component polyester fibers that have a fiber denier of about 6 d and that have fiber lengths of from about 3.8 to about 5.08 centimeters.

In the illustrated embodiments, the surge management layer 34 is arranged in a direct, contacting liquid communication with the absorbent body 24. The surge management layer 34 may be operably connected to the bodyside liner 22 with a conventional pattern of adhesive, such as a swirl adhesive pattern. In addition, the surge management layer 34 may be operably connected to the absorbent body 24 with a conventional pattern of adhesive. The amount of adhesive add-on should be sufficient to provide the desired levels of bonding, but should be low enough to avoid excessively restricting the movement of liquid from the bodyside liner 22, through the surge management layer 34 and into the absorbent body 24.

The absorbent body 24 is positioned in liquid communication with surge management layer 34 to receive liquids released from the surge management layer 34, and to hold and store the liquid. In the shown embodiment, the surge management layer 34 includes a separate layer that is positioned over another, separate layer including the absorbent body 24, thereby forming a dual-layer arrangement. The surge management layer 34 serves to quickly collect and temporarily hold discharged liquids, to transport such liquids from the point of initial contact and spread the liquid to other parts of the surge management layer 34, and then to substantially completely release such liquids into the layer or layers constituting the absorbent body 24.

The surge management layer 34 can be of any desired shape. Suitable shapes include for example, circular, rectangular, triangular, trapezoidal, oblong, dog-boned, hourglass-shaped, or oval. In certain embodiments, for example, the surge management layer 34 can be generally rectangular-shaped. In the illustrated embodiments, the surge management layer 34 is coextensive with the absorbent body 24. Alternatively, the surge management layer 34 may extend over only a part of the absorbent body 24. Where the surge management layer 34 extends only partially along the length of the absorbent body 24, the surge management layer 34 may be selectively positioned anywhere along the absorbent body 24. For example, the surge management layer 34 may function more efficiently when it is offset toward the front waist section 12 of the diaper 10. The surge management layer 34 may also be approximately centered about the longitudinal center line of the absorbent body 24.

Additional materials suitable for the surge management layer 34 are set forth in U.S. Pat. No. 5,486,166 issued Jan. 23, 1996 in the name of C. Ellis et al. and entitled "FIBROUS NONWOVEN WEB SURGE LAYER FOR PERSONAL CARE ABSORBENT ARTICLES AND THE LIKE"; U.S. Pat. No. 5,490,846 issued Feb. 13, 1996 in the name of Ellis et al. and entitled "IMPROVED SURGE MANAGEMENT FIBROUS NONWOVEN WEB FOR PERSONAL CARE ABSORBENT ARTICLES AND THE LIKE"; and U.S. Pat. No. 5,364,382 issued Nov. 15, 1994 in the name of Latimer et al. and entitled "ABSORBENT STRUCTURE HAVING IMPROVED FLUID SURGE MANAGEMENT AND PRODUCT INCORPORATING SAME", the disclosures of which are hereby incorporated by reference.

As representatively illustrated in FIG. 1, the diaper 10 may also include a ventilation layer 32 located between the outer cover 20 and the absorbent body 24. The ventilation layer 32 serves to facilitate the movement of air within and through the diaper 10 and prevent the outer cover 20 from being in surface to surface contact with at least a portion of the absorbent body 24. Specifically, the ventilation layer 32 serves as a conduit through which air and water vapor can move from the absorbent body 24 through the vapor permeable outer cover 20.

The ventilation layer 32 may be formed from materials described above as being suitable for the surge management layer 34 such as nonwoven, (e.g., spunbond, meltblown or carded), woven, or knitted fibrous webs composed of natural fibers and/or synthetic polymeric fibers. Suitable fibers include, for example, acrylic fibers, polyolefin fibers, polyester fibers, or blends thereof. The ventilation layer 32 may also be formed from a porous foam material such as an open-celled polyolefin foam, a reticulated polyurethane foam, and the like. The ventilation layer 32 may include a single layer of material or a composite of two or more layers of material. In a particular embodiment, the ventilation layer 32 includes a hydrophobic, nonwoven material having a thickness of at least about 0.10 centimeters determined under a restraining pressure of 0.05 psi (0.34 kPa) and a basis weight of from about 20 to about 120 grams per square meter. For example, the ventilation layer 32 may comprise a bonded-carded-web, nonwoven fabric that includes bicomponent fibers and that defines an overall basis weight of about 83 grams per square meter. The ventilation layer 32 in such a configuration can be a homogeneous blend composed of about 60 weight percent polyethylene/polyester (PE/PET), sheath-core bicomponent fibers that have a fiber denier of about 3 d and about 40 weight percent single component polyester fibers that have a fiber denier of about 6 d and that have fiber lengths of from about 3.8 to about 5.08 centimeters.

The ventilation layer 32 can be of any desired shape. Suitable shapes include for example, circular, rectangular, triangular, trapezoidal, oblong, dog-boned, hourglass-shaped, or oval. The ventilation layer 32 may extend beyond, completely over or partially over the absorbent body 24. For example, the ventilation layer 32 may suitably be located over the intermediate section 16 of the diaper 10 and be substantially centered side-to-side with respect to the longitudinal centerline 36 of the diaper 10. It is generally desired that the entire absorbent body 24 be overlaid with the ventilation layer 32 to prevent substantially all surface to surface contact between the outer cover 20 and the absorbent body 24. In the illustrated embodiments, the ventilation layer 32 is coextensive with the absorbent body 24. This allows for the maximum degree of air exchange with minimal dampness on the garment facing surface of the outer cover 20.

In the illustrated embodiments, the ventilation layer 32 is arranged in a direct, contacting liquid communication with the absorbent body 24. The ventilation layer 32 may be operably connected to the outer cover 20 with a conventional pattern of adhesive, such as a swirl adhesive pattern. In addition, the ventilation layer 32 may be operably connected to the absorbent body 24 with a conventional pattern of adhesive. The amount of adhesive add-on should be sufficient to provide the desired levels of bonding, but should be low enough to avoid excessively restricting the movement of air and vapor from the absorbent body 24 and through the outer cover 20.

The ventilation layer 32 may further serve to quickly collect and temporarily hold discharged liquids, which pass through the absorbent body 24 and, in particular, through the zones of high air permeability within the absorbent body 24. The ventilation layer 32 may then transport such liquids from the point of initial contact and spread the liquid to other parts of the ventilation layer 32, and then substantially completely release such liquids into the layer or layers of the absorbent body 24.

In order to maintain and enhance the barrier of the skin covered by the diaper 10, a composition is applied to the bodyfacing surface 11 of the bodyside liner 22 of the diaper 10. The composition generally can include hydrophilic solvent(s), high molecular weight polyethylene glycol(s), fatty alcohol(s), emulsifying surfactant(s), natural fats or oils, sterols or sterol derivatives and emollient(s). The composition can optionally include one or more viscosity enhancers or rheology modifiers. For example, the compositions of the invention may include from about 10 to about 90 percent by weight of one or more hydrophilic solvents; from about 5 to about 95 percent by weight of one or more high molecular weight polyethylene glycols; from about 1 to about 30 percent by weight of one or more fatty alcohols; from about 1 to about 20 percent by weight of one or more emulsifying surfactants; from about 0.1 to about 30 percent by weight of one or more natural fats or oils; from about 0.1 to about 10 percent by weight of one or more sterols or sterol derivatives; and from about 0.1 to about 10 percent by weight of one or more emollients. The composition may include other ingredients as well. Ranges are used to describe the relative amounts of components in the compositions of the invention as well as to describe the relative physical properties of the compositions. These ranges are illustrative and one of skill in the art will recognize that the nature of the composition will dictate the various levels of components that must be used to achieve the intended benefit for the skin barrier. The levels can be determined by routine experimentation in view of the disclosure provided herein.

The compositions of the invention can be in a variety of physical forms including emulsions, lotions, creams, ointments, salves, suspensions, encapsulations, gels or hybrids of these forms.

The compositions of the invention can include one or more hydrophilic solvents. The hydrophilic solvents provide the "backbone" for the hydrophilic characteristics of the compositions. The hydrophilic solvents give the compositions their overall "hydrophilic" nature and provide the attraction for water and other water-containing molecules. The hydrophilic solvents impart the ability of the entire composition to act as a carrier for bringing lipids into the skin barrier. Hydrophilic solvents include, but are not limited to, water, propylene glycol, low molecular weight polyethylene glycols (molecular weights of less than 720 and liquid at room temperature), methoxyisopropanol, PPG-2 propyl ether, PPG-2 butyl ether, PPG-2 methyl ether, PPG-3 methyl ether, dipropylene glycol propyl ether, dipropylene glycol butyl ether, dipropylene glycol, methyl propanediol, propylene carbonate, water soluble/dispersible polypropylene glycols, ethoxylated polypropylene glycol, glycerin, sorbitol solutions, hydrogenated starch hydrolysate, silicone glycols and mixtures of such compounds. The compositions can include from about 10 to about 90 percent by weight of one or more hydrophilic solvents. More specifically, the compositions can include from about 25 to about 75 percent by weight of hydrophilic solvents. Desirably, the compositions of the invention can include from about 30 to about 60 percent by weight of hydrophilic solvents.

The compositions of the invention can also include one or more high molecular weight polyethylene glycols. The high molecular weight polyethylene glycols primarily function to provide the hydrophilic solvents and any active ingredients in solid form at room temperature. The high molecular weight polyethylene glycols also contribute the composition having a penetration hardness of at least 5 mm. In addition to providing a solid medium for the solvent, and reducing its tendency to migrate, the high molecular weight polyethylene glycols provide a tackiness to the hydrophilic lotion composition that improves transfer to the skin of the wearer. As used herein, suitable high molecular weight polyethylene glycols include, but are not limited to, the following materials: polyethylene glycols having an average molecular weight of 720 daltons or greater and mixtures of such glycols. These materials are not liquid at room temperature. Particularly suitable high molecular weight polyethylene glycols can have an average molecular weight of from 720 to about 1,840,000 daltons, more specifically from about 1400 to about 440,000 daltons, and still more specifically from about 1760 to about 10,570 daltons. The compositions of the invention include from about 5 to about 95 percent by weight of one or more high molecular weight polyethylene glycols. More specifically, the compositions can include from about 10 to about 50 percent by weight of high molecular weight polyethylene glycols. Desirably, the compositions of the invention can include from about 15 to about 25 percent by weight of high molecular weight polyethylene glycols.

The compositions of the invention further include one or more fatty alcohols. The fatty alcohols, combined with the high molecular weight polyethylene glycols, provide the solid form for the compositions at room temperature. The fatty alcohols also contribute to the composition having a penetration hardness of at least 5 mm. The fatty alcohols contribute to the solid nature of the compositions and, thereby, assist in maintaining and stabilizing the compositions on the bodyfacing surface 11 of the bodyside liner 22. Suitable fatty alcohols include, but are not limited to, the following materials: alcohols having a carbon chain length of $C_{14}$–$C_{30}$ or greater, including cetyl alcohol, stearyl alcohol, arachidyl alcohol, behenyl alcohol, and mixtures thereof. The compositions of the invention include from about 1 to about 30 percent by weight of one or more fatty alcohols. More specifically, the compositions can include from about 10 to about 25 percent by weight of fatty alcohols. Desirably, the compositions of the invention can include from about 15 to about 20 percent by weight of fatty alcohols.

The compositions of the invention also include one or more emulsifying surfactants, including oil-in-water emulsifying surfactants. The surfactants provide for the incorporation of lipid (fats, oils, sterols and sterol derivatives, etc.) and other (emollient) components of the composition into the hydrophilic solvent(s). By emulsifying the lipid and other components into the hydrophilic solvent(s), the surfactants contribute to the delivery of the lipids and other beneficial compounds to the skin barrier. Emulsifying surfactants are employed typically in cosmetic preparations to form emulsions of various components. The immiscible phase, such as an oil, is dispersed as droplets in the continuous phase, such as water or in this case the hydrophilic solvent. Suitable surfactants include, but are not limited to, Emulsifying Wax NF, Glyceryl Stearate, Glyceryl Stearate SE, Glycol Stearate, Glycol Stearate SE, Glycereth-20 Stearate, Glyceryl Behenate, Glyceryl Hydroxystearate, Glyceryl Laurate SE, Glyceryl Oleate, Glyceryl Oleate SE, Propylene Glycol Oleate, Propylene Glycol Oleate SE, Propylene Glycol Stearate, Propylene Glycol Stearate SE, Sorbitan Stearate, Sorbitan Trioleate, water dispersible metal soaps (Sodium Stearate), Behenyl Dimethicone Copolymers, Lauryl Methicone Copolymers, Cetyl Methicone Compolymers, Cetyl Dimethicone Copolymers, Stearyl Dimethicone Copolymers, Dimethicone Copolymers and mixtures thereof. The surfactants of the composition may also be characterized as having a combined HLB in a range greater than 7. Therefore, one or more surfactants can be selected for use in the composition and their combined HLB would be in a range greater than 7. The compositions of the invention include from about 1 to about 20 percent by weight of one or more emulsifying surfactants having a combined HLB in a range greater than 7. More specifically, the compositions can include from about 2 to about 15 percent by weight of surfactants. Desirably, the compositions of the invention can include from about 3 to about 10 percent by weight of surfactants.

The compositions of the invention can also include fats and oils that provide a source of essential and non-essential fatty acids similar to those found in the skin's natural barrier. Fats and oils include compounds that are fats, oils, essential oils, fatty acids, fatty alcohols, phospholipids and mixtures of such compounds. Fats and oils include oils derived from plant and animal sources. Similarly, the essential oils include essential oils derived from plant sources. Those of skill in the art would understand that all compounds commonly understood to have the structure of or to function as fats, oils, essential oils, fatty acids, fatty alcohols and phospholipids can be used as the natural fat or oil component of the composition of the invention. While an exhaustive list of each and every fat and oil that could be used in the compositions of the invention is not provided, those of skill in the art will understand and appreciate the individual compounds that can serve as a fat or oil component of the compositions of the invention.

Representative examples of fats and oils include, but are not limited to: Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lanolin, Lanolin Alcohol, Lauric Acid, Palmitic Acid, Stearic Acid, Linoleic Acid, Stearyl Alcohol, Lauryl Alcohol, Myristyl Alcohol, Benenyl Alcohol, Rose Hip Oil, Calendula Oil, Chamomile Oil, Eucalyptus Oil, Juniper Oil, Sandlewood Oil, Tea Tree Oil, Sunflower Oil, and Soybean Oil. Another suitable fat/oil for the compositions of the invention is PROLIPID 141 blend available from International Specialty Products of Wayne, N.J. The PROLIPID 141 blend is a mixture of glyceryl stearate, fatty acids, fatty alcohols and phospholipids.

In order to assist in replenishing skin barrier enhancing agents, the compositions of the invention may include fats and oils in an amount of from about 0.1 to about 30 percent by weight, desirably from about 0.5 to about 25 percent by weight, and more desirably from about 1 to about 20 percent by weight of the composition.

The compositions of the invention also include sterols and sterol derivatives that act in combination with the natural fats/oils to provide natural skin barrier enhancement and skin barrier recovery. Sterols and sterol derivatives that can be used in the compositions of the invention include, but are not limited to: β-sterols having a tail on the 17 position and having no polar groups for example, cholesterol, sitosterol, stigmasterol, and ergosterol, as well as, $C_{10}$–$C_{30}$ cholesterol/ lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, "AVOCADIN" (trade name of Croda Ltd. of Parsippany, N.J.), sterol esters, and similar compounds, as well as mixtures thereof. The compositions of the invention can include sterols, sterol derivatives or mixtures of both sterols and sterol derivatives in an amount of from about 0.1 to about 10 percent by weight, desirably from about 0.5 to about 5 percent by weight and more desirably from about 0.8 to about 3 percent by weight of the composition.

To provide improved stability and transfer to the skin of the wearer, the compositions may include one or more emollients. The emollients of the compositions act as lubricants to reduce the abrasiveness of the bodyside liner 22 to the skin and, upon transfer to the skin, help to maintain the soft, smooth and pliable appearance of the skin. The compositions of the invention can include from about 0.1 to about 10 percent by weight of one or more emollients. More specifically, the compositions include from about 0.5 to about 5 percent by weight of emollient(s). Even more specifically, the compositions include from about 1 to about 5 percent by weight of emollient(s). Suitable emollients include petroleum based oils, petrolatum, vegetable oils, mineral oils, alkyl dimethicones, alkyl methicones, alkyldimethicone copolyols, phenyl silicones, alkyl trimethylsilanes, dimethicone, lanolin and its derivatives, fatty esters, glycerol esters and their derivatives, propylene glycol esters and their derivatives, alkoxylated carboxylic acids, alkoxylated alcohols, fatty alcohols and mixtures of such compounds.

The compositions of the invention can include the emollient and skin protectant, dimethicone. The dimethicone can be blended with the other components of the composition through the addition of water-based emulsions containing dimethicone such as emulsions having the trade designations "Dow Corning 1669 Emulsion" and "Dow Corning 1664 Emulsion" available from Dow Corning of Midland, Mich. The dimethicone can also be blended using a microencapsulated dimethicone such as are available from Lipo Technologies of Dayton, Ohio or from 3M of St. Paul, Minn. The dimethicone can also be added to the compositions of the invention in the form of an entrapped dimethicone. Dimethicone can be entrapped in "Polytrap" or "Microsponges" as are available from Advanced Polymer Systems of San Francisco, Calif. The dimethicone can also be incorporated in the form of a dimethicone treated powder such as dimethicone-treated talc or dimethicone-treated zinc oxide as are available from KOBO of South Plainfield, N.J.

The water-based emulsions containing dimethicone can be included in the composition in an amount of from about 2 to about 10 percent by weight. The microencapsulated dimethicone can be added to the composition in an amount of from about 4 to about 20 percent by weight. Forms of entrapped dimethicone can be added to the composition in amounts of from about 2 to about 20 percent by weight. The dimethicone treated powders can be added in amounts of from about 5 to about 20 percent by weight.

Compositions of the invention in which dimethicone and similar siloxane compounds are used as emollients provide a beneficial skin protecting effect. However, dimethicone and the other siloxane compounds require a surfactant in order to disperse them into the hydrophilic solvent of the compositions. The siloxane compounds can be introduced into the composition in at least two different ways. The first approach involves dispersing the siloxane in the lipid components of the composition before they are blended with the hydrophilic components. The siloxane can be dispersed either by itself or using an emollient ester into a blend of the lipid (fats/oil, sterols, etc.) components of the composition. A surfactant mixture having an HLB greater than 7 is then added to the lipid/siloxane components before they are combined with the hydrophilic components. The second approach involves emulsifying the siloxane into a mixture of the hydrophilic components using a suitable blend of surfactants (either all organic surfactants, alkyl silicone copolymers or a blend of organic surfactants and alkyl silicone copolymers) having an HLB greater than 7. The siloxane is blended with the surfactants and then the siloxane/surfactant mixture is added to the hydrophilic components.

Contrary to the need for surfactants to incorporate siloxane compounds, dimethicone in other forms does not require a surfactant. The dimethicone emulsions, encapsulated dimethicone, entrapped dimethicone and dimethicone-treated powders can all be dispersed into the compositions of the invention after all of the other components have been blended.

Optionally, the compositions of the invention may include from about 1 percent by weight to about 20 percent by weight of one or more viscosity enhancers or rheology modifiers. The viscosity enhancers and rheology modifiers can be added to increase the melt point viscosity of the compositions. Increasing the melt point viscosity gives better stability of the compositions on the bodyfacing materials of the articles. The viscosity enhancers and rheology modifiers also improve the stability of the composition at a "hot box car" stability temperature of about 130° F. (54.5° C.). Suitable viscosity enhancers can include, but are not limited to, Actrylamides Copolymers, Agar, Gelatin, Water-Dispersable Metal Soaps, Butoxy Chitosan, Calcium Carboxymethyl Cellulose, Calcium Alginate, Carbomer, Carboxybutyl Chitosan, Carboxymethyl Chitosan, Carboxymethyl Dextran, Carboxymethyl Hydroxyethyl Cellulose, Cellulose Gum, DMAPA Acrylates/Acrylic Acid/ Acrylonitrogens, Hectorite, Hydrated Silica, Hydroxyethyl Cellulose, Hydroxypropyl Guar, Hydroxypropyl Methylcellulose, Isobutylene/Sodium Maleate Copolymer, Kelp, Lithium Magnesium Silicate, Lithium Magnesium Sodium Silicate, Magnesium/Aluminum/Hydroxide/ Carbonate, Magnesium Aluminum Silicate, Magnesium Silicate, Magnesium Trisilicate, Methoxy PEG-22/Dodecyl Glycol Copolymer, Methyl Cellulose, Methyl Hydroxyethylcellulose, Microcrystalline Cellulose, Montmorillonite, Nonoxynol Hydroxyethylcellulose, PEG Crosspolymer, Polyacrylate-3, Polyacrylic Acid, Polyethylene/isopropyl Maleate Copolymer, Polymethacrylic Acid, Polyvinyl Alcohol, PVP/Decene Copolymer, PVP Montmorillonite, Sodium Acrylates Copolymer, Sodium Acrylate/Vinyl Alcohol Copolymer, Sodium Acrylates/Vinyl Isodecanate Crosspolymer, Sodium Carboxymethyl Starch, Sodium Hydroxypropyl Starch Phosphate, Sodium Polyacrylate, TEA Alginate, TEA Carbomer, Xanthan Gum, Yeast Polysaccharides and mixtures thereof.

If it is desired that the composition provide a treatment for the skin, the composition can also include an active ingredient such as a diaper rash skin protectant. Skin protectants are drug products that protect injured or exposed skin or mucous membrane surface from harmful or annoying stimuli. Suitable active ingredients, in addition to those mentioned above as suitable emollients, that can be incorporated into the composition include, but are not limited to, allantoin and its derivatives, aluminum hydroxide gel, calamine, cocoa butter, dimethicone, cod liver oil, kaolin and its derivatives, lanolin and its derivatives, mineral oil, petrolatum, shark liver oil, talc, topical starch, zinc acetate, zinc carbonate, zinc oxide and mixtures thereof. The composition may include from about 0.10 to about 95 percent by weight of the active ingredient depending upon the skin protectant, the amount desired to be transferred to the skin and the amount required in a particular FDA skin protectant monograph.

In order to better enhance the benefits to the wearer, additional ingredients can be included in the compositions of the present invention. For example, the classes of ingredients that may be used and their corresponding benefits include, without limitation: antifoaming agents (reduce the tendency of foaming during processing); antimicrobial actives; antifungal actives; antiseptic actives; antioxidants (product integrity); antioxidants-cosmetic (reduce oxidation); astringents-cosmetic (induce a tightening or tingling sensation on skin); astringent-drug (a drug product that checks oozing, discharge, or bleeding when applied to skin or mucous membrane and works by coagulating protein); biological additives (enhance the performance or consumer appeal of the product); colorants (impart color to the product); deodorants (reduce or eliminate unpleasant odor and protect against the formation of malodor on body surfaces); other emollients (help to maintain the soft, smooth, and pliable appearance of the skin by their ability to remain on the skin surface or in the stratum corneum to act as lubricants, to reduce flaking, and to improve the skin's appearance); external analgesics (a topically applied drug that has a topical analgesic, anesthetic, or antipruritic effect by depressing cutaneous sensory receptors, or that has a topical counterirritant effect by stimulating cutaneous sensory receptors); film formers (to hold active ingredients on the skin by producing a continuous film on skin upon drying); fragrances (consumer appeal); silicones/ organomodified silicones (protection, tissue water resistance, lubricity, tissue softness); oils (mineral, vegetable, and animal); natural moisturizing agents (NMF) and other skin moisturizing ingredients known in the art; opacifiers (reduce the clarity or transparent appearance of the product); powders (enhance lubricity, oil adsorption, provide skin protection, astringency, opacity, etc.); skin conditioning agents; solvents (liquids employed to dissolve components found useful in the cosmetics or drugs); and surfactants (as cleansing agents, emulsifying agents, solubilizing agents, and suspending agents).

An important property of the compositions of the different aspects of the present invention is their ability to remain on the surface of the bodyside liner 22 and their resistance to migration into the diaper 10 such that they can readily be transferred to the wearer's skin. In this regard, the articles having the compositions of the present invention applied to their bodyside liner 22 define a z-direction migration loss of no more than about 55%, desirably no more than about 50%, more desirably no more than about 45%, even more desirably no more than about 40% and yet even more desirably no more than about 35% when subjected to the Z-Direction Lotion Migration Test set forth below. In articles that have a greater z-direction migration loss, the composition undesirably migrates into the interior and along the surface of the bodyside liner 22 and at times through the bodyside liner 22 into the absorbent body 24 of the article which results in a lower reduction in abrasion and less transfer to the skin of the wearer.

Another important measure of the compositions of the different aspects of the present invention is their ability to resist migration laterally along the surface of the bodyside liner 22. In this regard, the articles having the compositions of the present invention applied to the bodyside liner 22 define a cd-direction migration loss of no more than about 40%, desirably no more than about 35%, more desirably no more than about 30%, even more desirably no more than about 25% and yet even more desirably no more than about 20% when subjected to the CD-Direction Lotion Migration Test set forth below. In articles which have a greater cd-direction migration loss, the composition undesirably migrates along the surface of the bodyside liner 22 and at times through the bodyside liner 22 into the absorbent body 24 of the article which results in a lower reduction in abrasion and less transfer to the skin of the wearer.

Moreover, to provide the improved stability and transfer to the skin of the wearer, the compositions of the present invention may define a melting point of from about 32° C. to about 100° C., desirably from about 35° C. to about 80° C., and more desirably from about 40° C. to about 75° C. Compositions that have lower melting points exhibit migration of the composition during use and at elevated temperatures in storage that can undesirably result in reduced transfer to the skin. Whereas, compositions that have higher melting points may require that the composition be at a temperature above the flash point of the bodyside liner 22 material which can undesirably lead to fires. The melting points of the compositions of the invention cause the compositions to be relatively immobile and localized on the bodyfacing surface 11 of the diaper 10 at room temperature and readily transferable to the skin of the wearer at body temperatures. However, the compositions of the invention are not completely liquid under extreme storage conditions. Stability in a solid state at elevated temperatures is made possible, in part, by the melting point and the rheology provided by the high molecular weight polyethylene glycol and the addition of viscosity enhancers/rheology modifiers, if needed, in the composition. Desirably, the compositions are easily transferable to the skin by way of normal contact, wearer motion, adhesion or body heat. When the compositions are relatively immobilized at room temperature, a lesser quantity of composition is required on the bodyfacing surface 11 to provide a beneficial effect.

The composition of the present invention may further define a "hot box car" stability viscosity of from about 200 to about 1,000,000 centipoise, desirably from about 50,000 to about 800,000 centipoise, and more desirably from about 100,000 to about 500,000 centipoise for reduced migration and improved transfer to the skin of the wearer. Compositions that have lower melt point viscosities exhibit migration of the composition through the bodyside liner 22 into the absorbent body 24 of the article which can undesirably result in reduced transfer to the skin. Whereas, compositions that have higher melt point viscosities may be so solid as to also exhibit a reduced transfer to the skin.

Further, to provide the improved stability and transfer to the skin of the wearer, the composition of the present invention may also define a viscosity of from about 50 to about 10,000 centipoise, desirably from about 100 to about 500 centipoise, and more desirably from about 150 to about 250 centipoise at a temperature of 60° C. The compositions of the invention can have a process viscosity of 100 centipoise or less under shear or pressure.

The penetration hardness of the compositions of this invention can be from about 5 to about 365 millimeters, more desirably from about 10 to about 300 millimeters, more desirably from about 20 to about 200 millimeters, and still more desirably from about 40 to about 120 millimeters. (Compositions having a needle penetration hardness greater than 365 millimeters cannot be measured using ASTM method D 1321). The hardness of the compositions of this invention is important for two reasons. First, the softer the formulation the more mobile the formulation will be, making the formulation more likely to migrate to the inner plies of the diaper 10, which is not desirable. Secondly, softer compositions tend to be more greasy/oily to the touch, which is also less desirable. In general, compositions having a needle penetration hardness of from about 200 to about 365 millimeters feel creamy to slightly greasy with less smoothness (depending on additives). Compositions that have needle penetration hardness values of from about 5 to about 200 millimeters feel silky to creamy and very smooth (depending on additives).

Figure 3:
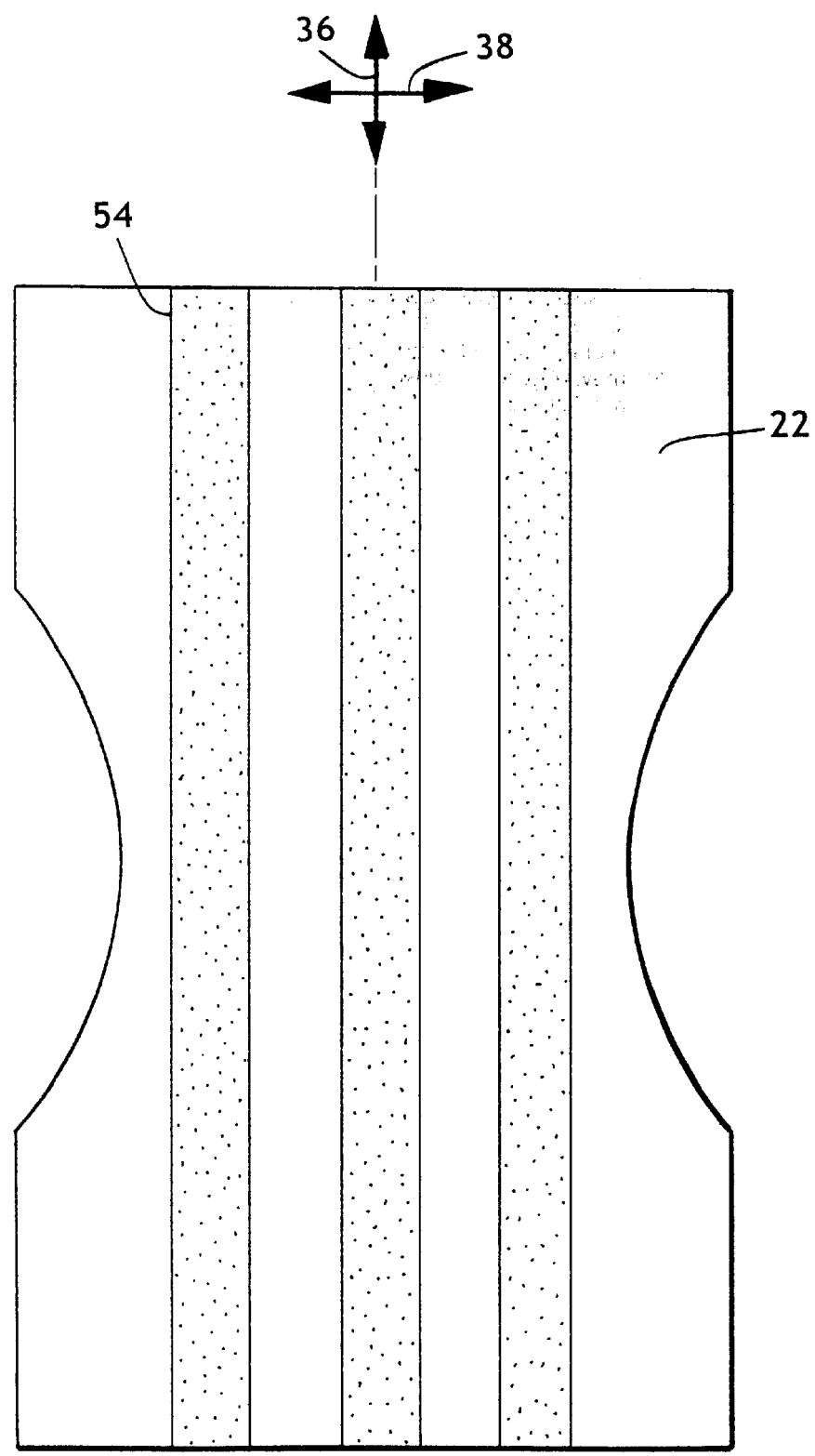
FIG. 3 representatively shows a top plan view of the bodyside liner of the absorbent article of FIG. 1 with the surface that contacts the wearer facing the viewer.

The composition may be applied to the entire bodyfacing surface 11 of the bodyside liner 22 or may be selectively applied to particular sections of the bodyfacing surface 11, such as the medial section along the longitudinal centerline of the diaper 10, to provide greater lubricity of such sections and to transfer such composition to the wearer's skin. Alternatively, the bodyfacing surface 11 of the bodyside liner 22 may include multiple stripes of the composition applied thereto as illustrated in FIG. 3. For example, the bodyfacing surface 11 of the bodyside liner 22 may include from 1 to 20 stripes 54 of composition extending along the longitudinal direction of the diaper 10. The stripes 54 may extend the full length of the bodyside liner 22 or only a portion thereof. The stripes 54 may also define a width of from about 0.2 to about 1 centimeters.

The composition should cover a sufficient amount of the bodyfacing surface 11 of the bodyside liner 22 to ensure adequate transfer to the skin and reduced abrasion between the bodyside liner 22 and the wearer's skin. Desirably, the composition is applied to at least about 5 percent and more desirably at least about 25 percent of the bodyfacing surface 11 of the bodyside liner 22.

The composition can be applied to the bodyside liner 22 at any add-on level that provides the desired transfer benefit. For example, the total add-on level of the composition can be from about 0.05 to about 100 mg/cm$^2$, desirably from about 1 to about 50 mg/cm$^2$ and more desirably from about 10 to about 40 mg/cm$^2$ for improved performance. The add-on amount will depend upon the desired effect of the composition on the skin barrier function and the specific composition. As discussed above, the improved stability and reduced tendency to migrate of the compositions of the present invention allows a lesser amount of composition to be applied to the bodyside liner 22 to achieve the same benefit when compared with conventional compositions.

The composition may be applied to the bodyside liner 22 in any of many well known manners. A preferred method to uniformly apply the composition to the bodyfacing surface 11 of the bodyside liner 22 is spraying or slot coating. Spraying or slot coating the composition is the most exact process and offers maximum control of the composition distribution and transfer rate. However, other methods, such as roto-gravure or flexographic printing and foam application can be used. The compositions of the present invention can be applied after the bodyfacing material has been incorporated into the absorbent article or prior to incorporating the body facing material into the absorbent article.

The composition may be applied to the bodyside liner 22 by (a) heating the composition to a temperature above the melting point of the composition, causing the composition to melt, (b) uniformly applying the melted composition to the bodyfacing surface 11 of the bodyside liner 22; and (c) resolidifying the composition applied to the bodyfacing surface 11. Desirably, resolidification of the composition occurs almost instantaneously, without the need for external cooling devices such as chill rolls. This can occur if the composition is heated to a temperature only slightly above or at the melting point of the composition. However, external cooling devices such as chill rolls, either before or after the application of melt, can be used if desired to accelerate resolidification. Other cooling methods such as cooling tunnels could also be used. After resolidification, the composition typically has a static viscosity of greater than about 200 centipoise. Further, the composition can have a penetration hardness of from about 5 to about 365 millimeters at 25° C.

The increased viscosity of the composition at the process temperature and the instantaneous resolidification tends to impede penetration of the composition into the bodyside liner 22 and absorbent body 24 of the diaper 10 and retain it on the bodyfacing surface 11 of the bodyside liner 22, which is advantageous. For example, the temperature of the melted composition can advantageously be less than about 10° C., more desirably less than about 5° C., and still more desirably less than about 2° C. above the melting point of the composition prior to applying it to the bodyside liner 22 for reduced migration. As the temperature of the melted composition approaches the melting point of the composition, the viscosity of the melted composition generally increases, which further enhances the tendency of the melted composition to be retained on the bodyfacing surface 11.

In an example of the method of the invention, the hydrophilic solvent phase is prepared first. First, the hydrophilic solvent is heated to a temperature of from about 2 to about 5° C. above the melting point of the high molecular weight polyethylene glycols and the fatty alcohols that have been selected for use in the composition to be applied to the bodyfacing surface 11. Next, the high molecular weight polyethylene glycol and fatty alcohol components are added to the hydrophilic solvent and the mixture is agitated until melted. Other hydrophilic components and, if desired, the viscosity enhancer/rheology modifier component are added and the mixture is agitated until it is uniform or all of the components are dispersed. The mixture is cooled to a temperature of about 5° C. above the freezing point of the composition. Separately, the natural fat/oil component is heated to about 90° C. and the sterol component is added. The lipid blend is mixed until melted. The emollient component, including dimethicone, if desired, is then added to the lipid blend. The lipid blend is then cooled to a temperature of about 5° C. above the freezing point of the composition and the emulsifying surfactants are added. The lipid blend is then mixed until it is uniform. With good agitation, the lipid blend is then added to the hydrophilic solvent mixture. High shear may be necessary to finely disperse the lipid blend and high shear will also reduce the particle size of the emulsion droplets. The composition can then be applied to the bodyfacing surface 11 of the bodyside liner 22 of the article.

The present invention is also directed to an absorbent article, such as a diaper 10, that includes an outer cover 20, a liquid permeable bodyside liner 22, an absorbent body 24 and a composition. The bodyside liner 22 defines a bodyfacing surface 11. As already described herein, the bodyfacing surface 11 is that portion of the article that comes into contact with the skin of the wearer or user of the article. When the article is a diaper 10, the bodyfacing surface 11 typically is primarily the bodyside liner 22, but the bodyfacing surface 11 can also include waist and leg elastics 26, 28, containment flaps and fasteners 30. When the article is a primarily two-dimensional substrate such as a tissue or wet wipe, the entire surface area of the tissue or wet wipe is the bodyfacing surface 11 as any portion of such articles may contact the user's skin.

The bodyside liner 22 is in superposed relation to the outer cover 20. The absorbent body 24 is located between the bodyside liner 22 and the outer cover 20. At least a portion of the bodyfacing surface 11 of the bodyside liner 22 has a composition on it. The composition includes from about 25 to about 75 percent by weight of hydrophilic solvent. The hydrophilic solvent can be selected from water, propylene glycol, low molecular weight polyethylene glycols (molecular weights of less than 720 and liquid at room temperature), water soluble/dispersible polypropylene glycols, ethoxylated polypropylene glycol, glycerin, sorbitol solutions, hydrogenated starch hydrolysate, silicone glycols and mixtures of such compounds. The composition also includes from about 10 to about 50 percent by weight of high molecular weight polyethylene glycol having a molecular weight of at least about 720 daltons. The composition includes from about 10 to about 25 percent by weight of $C_{14}$ to $C_{30}$ or greater fatty alcohol. The composition also includes from about 2 to about 15 percent by weight of emulsifying surfactant having a combined HLB in a range greater than 7. The emulsifying surfactant can be selected from Emulsifying Wax NF, Glyceryl Stearate, Glycol Stearate, Glyceryl Behenate, Glyceryl Hydroxystearate, Glyceryl Laurate SE, Glyceryl Oleate, Propylene Glycol Oleate, Propylene Glycol Stearate, Sorbitan Stearate, Sorbitan Trioleate, water dispersible metal soaps (Sodium Stearate), Behenyl Dimethicone Copolymers, Lauryl Methicone Copolymers, Cetyl Methicone Compolymers, Cetyl Dimethicone Copolymers, Stearyl Dimethicone Copolymers, Dimethicone Copolymers and mixtures thereof. The composition includes from about 0.5 to about 25 percent by weight of natural fats or oils. The natural fats and oils can be selected from avocado oil, borage oil, sunflower oil, soybean oil, corn oil, cottonseed oil, sweet almond oil and mixtures of these compounds. The composition also includes from about 0.5 to about 5 percent by weight of sterols or sterol derivatives. The sterols and sterol derivatives can be selected from cholesterol, sitosterol, stigmasterol, tall oil sterol, soy sterol and mixtures of these compounds. Additionally, the composition includes from about 0.1 to about 10 percent by weight of one or more emollients. The emollients can be selected from petroleum based oils, petrolatum, vegetable oils, mineral oils, alkyl dimethicones, alkyl methicones, alkyldimethicone copolyols, phenyl silicones, alkyl trimethylsilanes, dimethicone, lanolin and its derivatives, fatty esters, alkoxylated alcohols, fatty alcohols and mixtures of these compounds. Optionally, the composition can also include from about 1 to about 20 percent by weight of one or more viscosity enhancers or rheology modifiers.

The composition has physical properties that are suitable to provide a relative degree of immobilization on the bodyfacing surface 11 at room temperature and to provide sufficient fluid or transfer properties at body temperature so that the composition can migrate to the skin. Typically, the composition has a melting point of from about 32° C. to about 100° C. and a viscosity of from about 10 to about 10,000 centipoise at a temperature of 60° C. The composition may also have a penetration hardness of from about 5 millimeters to about 365 millimeters at 25° C. The composition is typically present on the bodyfacing surface 11 in an amount of from about 0.1 $g/m^2$ to about 30 $g/m^2$. The composition applied to the bodyfacing surface 11 may have additional ingredients added to it in order to provide additional benefits or to enhance the functionality and processability of the composition.

The present invention is also directed to a method of applying a composition to a bodyfacing surface 11 of a bodyside liner 22 of an absorbent article. The method includes a step of heating a composition to a temperature above the melting point of the composition. The composition generally enhances the skin barrier function and can include a hydrophilic solvent, high molecular weight polyethylene glycol, fatty alcohol, oil-in-water emulsifying surfactant or surfactant combination, natural fat or oil, a sterol or sterol derivative and an emollient. The composition can optionally include one or more viscosity enhancers or rheology modifiers. The melting point of the composition is from about 32° C. to about 100° C. The method also includes a step of applying the composition to the bodyfacing surface 11 of a bodyside liner 22 of an absorbent article. The method further includes a step of resolidifying the composition. The composition can be applied to the bodyfacing surface 11 using any of the techniques already describe herein such as foam application, spraying, slot coating and printing. The composition can be resolidified using devices that are commonly used for cooling, such as chill rolls and cooling tunnels, or the composition can be resolidified by selecting a combination of ingredients that puts the melting point close to the processing temperature. When the melting point of the composition is close to the processing temperature, the composition should quickly resolidify after application to the bodyfacing surface 11. Typically, the composition has a static viscosity of greater than about 200 centipoise after resolidification. Further, the composition has a penetration hardness of from about 5 to about 365 millimeters at 25° C.

The present invention is further directed to a method for enhancing the barrier function of the skin. The method includes a step of contacting a skin surface of a user of an absorbent article with a bodyfacing surface 11 of a bodyside liner material. The method could also include a step of contacting the skin surface of a user of a tissue or wet wipe article with the outer surface of the material from which the tissue or wet wipe is constructed. The bodyfacing surface 11 or outer surface has a composition on it. The composition can include a hydrophilic solvent, a high molecular weight polyethylene glycol, a fatty alcohol, an oil-in-water emulsifying surfactant or other surfactant, a natural fat or oil, a sterol or sterol derivative and an emollient. The composition can also include one or more viscosity enhancers/rheology modifiers. The relative amounts and combinations of composition components can be varied. The method of the invention also includes a step of maintaining the bodyfacing surface 11 in contact with the skin surface of the user for a sufficient amount of time to transfer the composition to the skin surface. The amount of time is related to the nature of the composition and its physical properties; different compositions will transfer to a skin surface at different rates. The method further includes a step of repeating the maintaining step for a sufficient period of time to evidence enhancement of skin barrier function. Therefore, the method includes repeating the contact of the skin surface with the bodyfacing surface 11 of the liner material.

As suggested by the compositions already described herein, the composition applied to the bodyfacing surface 11 can include from about 10 to about 90 percent by weight of hydrophilic solvent, from about 5 to about 95 percent by weight of high molecular weight polyethylene glycol, from about 1 to about 30 percent by weight of a fatty alcohol, from about 1 to about 20 percent by weight of emulsifying surfactant, from about 0.1 to about 30 percent by weight of one or more natural fats and oils, from about 0.1 to about 10 percent by weight of one or more sterols or sterol derivatives and from about 0.1 to about percent by weight of one or more emollients. If desired, the composition can include from about 1 to about 20 percent by weight of one or more viscosity enhancers/rheology modifiers. Examples of suitable hydrophilic solvents, high molecular weight polyethylene glycols, fatty alcohols, emulsifying surfactants, fats and oils, sterols and sterol derivatives, emollients and viscosity enhancers/rheology modifiers are as described herein.

The descriptions of the articles and compositions of the invention provided herein have included references to various tests for assessing the attributes or properties of the components of the articles and compositions as well as the articles and compositions in their entireties. Descriptions of the test procedures used to make those assessments are now provided. cl Hydrostatic Pressure Test The Hydrostatic Pressure Test is a measure of the liquid barrier properties of a material. In general, the Hydrostatic Pressure Test determines the height of water (in centimeters) in a column that the material will support before a predetermined amount of water passes through. A material with a higher hydrohead value indicates it is a greater barrier to liquid penetration than a material having a lower hydrohead value. The Hydrostatic Pressure Test is performed according to Method 5514—Federal Test Methods Standard No. 191A.

Frazier Porosity Test

The Frazier Porosity values referred to in the present specification can be determined employing a Frazier Air Permeability Tester (Frazier Precision Instrument Co., Gaithersburg, Md.) and Method 5450, Federal Test Methods Standard No. 191A. For the purposes of the present invention, the test is conducted with a sample that measures 8 inches×8 inches.

Water Vapor Transmission Test

A suitable technique for determining the WVTR (water vapor transmission rate) value of a material is as follows.

For the purposes of the present invention, 3-inch diameter (76 millimeter) circular samples are cut from the test material and from a control material, CELGUARD 2500 material (Hoechst Celanese Corporation). Two or three samples are prepared for each material. Test cups used for testing are cast aluminum, flanged, 2 inches deep and come with a mechanical seal and neoprene gasket. The cups are distributed by Thwing-Albert Instrument Company, Philadelphia, Pa., under the designation "Vapometer cup #681". One hundred milliliters of distilled water are poured into each Vapometer cup, and each of the individual samples of the test materials and control material are placed across the open top area of an individual cup. Screw-on flanges are tightened to form a seal along the edges of the cups leaving the associated test material or control material exposed to the ambient atmosphere over a 62 millimeter diameter circular area (an open, exposed area of about 30 cm$^2$). The cups are then weighed, placed on a tray, and set in a forced air oven set at 100° F. (38° C.). The oven is a constant temperature oven with external air circulating through it to prevent water vapor accumulation inside. A suitable forced air oven is, for example, a Blue M Power-O-Matic 60 oven distributed by Blue M Electric Co. of Blue Island, Ill. After 24 hours, the cups are removed from the oven and weighed. The preliminary, test WVTR value is calculated as follows:

$$\text{Test } WVTR = \frac{[(\text{grams weight loss over 24 hours}) \times 7571]}{24} \; (g/m^2/24 \text{ hours})$$

The relative humidity within the oven is not specifically controlled. Under predetermined set conditions of 100° F. and ambient relative humidity, the WVTR for CELGUARD 2500 materials has been determined to be 5000 g/m$^2$/24 hours. Accordingly, CELGUARD 2500 material is run as a control sample with each test. CELGUARD 2500 material is a 0.0025 cm thick film composed of a microporous polypropylene.

Z-Direction Composition Migration Test

This test determines the quantity of composition that remains on the target area of the bodyfacing surface of an absorbent article after a given period of time at a given temperature. Specifically, the purpose of the test is to compare the amount of composition present in the target zone on articles stored at a lower temperature with that present on articles stored at a higher temperature. The test simulates storage at elevated temperature conditions to which absorbent articles may be subjected. For example, such articles may be stored in the trunk of a vehicle or in a warehouse in a warm climate such as in a warehouse in Arizona in July or August. The z-direction migration loss is a measure of the composition migration after storage at 130° F. when compared to the composition migration at 73° F. after a fixed period of time. Thus, this test predicts the amount of composition that will be available on the bodyfacing surface of the article for transfer to the skin when the article is used as well as how quickly it will undesirably migrate away from or along the bodyfacing surface of the article in use.

Specifically, the test is conducted as follows:

1. Ten (10) products having a composition applied to the topsheet or bodyside liner are obtained.
2. Five (5) products are placed in a controlled environment at a temperature of 73° F. and a relative humidity of 50% for a fixed period of time such as, for example, 28 days. The other five (5) products are placed in a controlled environment at a temperature of 130° F. and ambient humidity for the same period of time.

3. The products are removed from the controlled environment and a sample of the bodyside liner having a width of 3.75 inches and a length of 13 inches is removed from the center of each product.

4. The samples are then subjected to Soxhlet Extraction with Gravimetric Analysis (SEGA) as follows. The test apparatus includes a reboiler, chloroform vapor duct, cold water condenser, holding tank where the samples are placed and a chloroform recycle duct. The components of the test apparatus are conventional glassware well known to those skilled in the art. For example, the reboiler may include a 250 ml round bottom flask and the vapor duct can include an 85 ml soxhlet. A sample is placed in the holding tank and subjected to chloroform washing cycles for 2.5 hours. One hundred twenty-five milliliters of liquid chloroform is placed in the reboiler. The chloroform vaporizes and rises up through the vapor duct into the condenser having tap water therein that, in turn, causes the chloroform to liquefy and fall into the holding tank with the sample. The chloroform dissolves the composition from the liner sample. When the liquid chloroform reaches a high enough level, the recycle duct returns the chloroform/composition mixture to the reboiler. The temperature in the reboiler is controlled such that it is above the boiling point of the chloroform but below that of the composition such that only the chloroform vaporizes to start the process over again. One complete wash cycle takes approximately minutes with about 75 milliliters of chloroform circulating through the liner sample in each cycle. Upon completion, the chloroform in the evaporator is evaporated utilizing a conventional vacuum evaporator such as a rotovap commercially available under the model number Buchi 011 RE 121 for a period of 4 minutes followed by placing the composition in an aluminum pan and heating on a hot plate with forced air circulation for an additional 30 minutes.

5. The residue (composition) remaining for each sample is then weighed. The amount of composition recovered from the products stored at 73° F. is then compared to the amount of composition recovered from the products stored at 130° F. to determine the stability of the composition formulation at high temperature.

The z-direction migration loss of the absorbent article is then determined as follows:

$$\text{Z-direction migration loss } (\%) = [(L_{73} - L_{130})/L_{73}] \times 100$$

wherein, $L_{73}$=average weight (g) of composition recovered per sample stored at 73° F.

$L_{130}$=average weight (g) of composition recovered per sample stored at 130° F.

CD-Direction Composition Migration Test

This test determines the quantity of composition that remains on the specific location where it is applied on the bodyfacing surface of an absorbent article after a given period of time at a given temperature. Specifically, the purpose of the test is to compare the amount of composition present in the applied location on the topsheet or bodyside liner with that present on the remaining portions of the bodyside liners of the articles after being stored at an elevated temperature. The test simulates storage at elevated temperature conditions to which absorbent articles may be subjected. For example, such articles may be stored in the trunk of a vehicle or in a warehouse in a warm climate such as in a warehouse in Arizona in July or August. The cd-direction migration loss is a measure of the lateral composition migration along the bodyfacing surface of the article after storage at 130° F. after a fixed period of time. Thus, this test predicts the amount of composition that will be available in the desired location on the bodyfacing surface of the article for transfer to the skin when the article is used as well as how quickly it will undesirably migrate away from or along the bodyfacing surface of the article in use.

Specifically, the test is conducted as follows:

1. Five (5) products having a composition applied to the bodyside liner in a specific pattern are obtained.

2. The products are placed in a controlled environment at a temperature of 130° F. and ambient humidity for a fixed period of time such as, for example, 28 days.

3. The products are removed from the controlled environment and the bodyside liner on each product is removed and dissected to remove the portion of the bodyside liner to which the composition was actually applied. For example, if the composition was applied as 4 continuous lines having a width of 0.25 inches with spaces of 0.75 inches in between, the 4 strips of bodyside liner would be removed.

4. The samples which include the portions of the bodyside liner to which the composition was applied are then grouped together and subjected to Soxhlet Extraction with Gravimetric Analysis (SEGA) as described above. The remaining portions of the bodyside liner are also grouped together and subjected to a separate SEGA extraction.

5. The residue (composition) remaining for each group is then weighed. The amount of composition recovered from the portions of the bodyside liner to which the composition was applied is then compared to the amount of composition recovered from the remaining portions of the bodyside liner to determine the stability of the composition at high temperature.

The cd-direction migration loss of the absorbent article is then determined as follows:

$$\text{CD-direction migration loss } (\%) = [L_{sp}/(L_a + L_{sp})] \times 100$$

wherein, $L_{sp}$=average weight (g) of composition recovered from the portions of the bodyside liner to which the composition was not applied per diaper $L_a$=average weight (g) of composition recovered from the portions of the bodyside liner to which the composition was applied per diaper The compositions of the present invention can be further described through examples of compositions considered to be within the scope of the present invention. The examples provided herein are intended to be representative of the present invention but are not intended to delineate the extent of the present invention. To the extent that amounts of individual components or total compositions are referred to in terms of "effective amounts", "effective amount" is understood to mean an amount that will have the desired effect of that component or composition. For example, an "effective amount" of one of the compositions of the invention is understood to mean an amount that, when applied to the bodyfacing or skin contacting surface of an article, will enhance the barrier function of the skin. Further, as used herein, all recited ranges of amounts, temperatures, molecular weights and penetration hardnesses are intended to include all sub-ranges within the recited ranges, even though not specifically stated. Examples of compositions of the invention are provided in Table 1. below.

TABLE 1

| Formula (weight percent) | 1 | 2 | 3 | 4 |
|---|---|---|---|---|
| Propylene Glycol | 43% | — | 49% | 36.50% |
| Polyethylene Glycol 200 | — | 40% | — | — |
| Methyl Propane Diol | — | — | 5% | 10% |
| Potyethylene Glycol 8000 | 20% | — | — | — |
| Polyethylene Glycol 10,000 | — | 18% | — | — |
| Polyethylene Glycol 20,000 | — | — | 15% | 20% |
| Cetyl Alcohol | — | — | 5% | — |
| Stearyl Alcohol | 10% | 5% | 18% | — |
| Behenyl Alcohol | 10% | 15% | — | 10% |
| Glyceryl Stearate SE | 3% | — | — | — |
| Emulsifying Wax NF | — | 5% | 3% | — |
| Glyceryl Laurate SE | — | — | — | 3.50% |
| Sunflower Oil | 10% | — | — | 10% |
| Borage Oil | — | 15% | — | — |
| Avocado Oil | — | — | 3% | — |
| Soy Sterol | 1% | — | — | — |
| Lanasterol | — | 2% | — | 10% |
| Cholesterol | — | — | 2% | — |
| Myristyl Myristate | 3% | — | — | — |

| Formula (weight percent) | 5 | 6 | 7 | 8 |
|---|---|---|---|---|
| Propylene Glycol | 28.20% | — | 75.50% | 5% |
| Methyl Propane Diol | — | 51% | — | 4% |
| Hydrogenated Starch Hydrolyzate | 5% | — | — | — |
| Polyethylene Glycol 6,000 | — | — | — | 25% |
| Polyethylene Glycol 10,000 | 25% | — | — | — |
| Polyethylene Glycol 15,000 | — | 20% | — | 15% |
| Polyethylene Glycol 50,000 | — | — | 5% | — |
| Cetyl Alcohol | — | 10% | — | — |
| Stearyl Alcohol | — | — | — | 15% |
| Behenyl Alcohol | 25% | 10% | 8% | — |
| Emulsifying Wax NF | — | 2% | — | 10% |
| Glyceryl Laurate SE | — | — | 3% | — |
| Laureth-3 | 2% | — | — | — |
| Laureth-4 | 3% | — | — | — |
| Cetyl Dimethicone Copolymer | — | — | 0.50% | — |
| Lauryl Methicone Copolymer | — | 1% | — | — |
| Dimethicone | 10% | 2% | 2% | 1% |
| Petrolatum | — | — | — | 5% |
| Sunflower Oil | 1% | — | — | 15% |
| Borage Oil | — | 3% | — | — |
| Avocado Oil | — | — | 5% | — |
| Soy Sterol | 0.80% | — | — | 5% |
| Lanasterol | — | — | 1% | — |
| Cholesterol | — | 1% | — | — |

| Formula (weight percent) | 9 | 10 | 11 | 12 |
|---|---|---|---|---|
| Propylene Glycol | 41% | — | 20% | 10% |
| Polyethylene Glycol 200 | — | 30% | — | 4% |
| Polyethylene Glycol 10,000 | 20% | 21% | 25% | 15% |
| Stearyl Alcohol | 10% | 10% | 10% | 15% |
| Behenyl Alcohol | 10% | 10% | 15% | 15% |
| Glyceryl Stearate SE | 3% | — | 15% | — |
| Emulsifying Wax NF | — | 5% | — | 10% |
| Sunflower Oil | 10% | — | 5% | 10% |
| Borage Oil | — | 15% | 10% | — |
| Cholesterol | 1% | 1% | 7% | 1% |
| DOW CORNING 1664 Emulsion | 5% | — | — | — |

TABLE 1-continued

| | | | | |
|---|---|---|---|---|
| Encapsulated Dimethicone | — | 8% | — | — |
| MICROSPONGE with Dimethicone | — | — | 3% | — |
| Dimethicone-treated Zinc Oxide | — | — | — | 20% |

While the invention has been described in detail with respect to the specific aspects thereof, it will be appreciated that those skilled in the art, upon attaining an understanding of the foregoing, may readily conceive of alterations to, variations of, and equivalents to these aspects. Accordingly, the scope of the present invention should be assessed as that of the appended claims and any equivalents thereto.

We claim:

1. An absorbent article comprising:
   (a) an outer cover;
   (b) a liquid permeable bodyside liner that defines a bodyfacing surface and that is connected in superposed relation to the outer cover;
   (c) an absorbent body that is located between the bodyside liner and the outer cover; and
   (d) a composition on at least a portion of the bodyfacing surface of the bodyside liner that includes from about 10 to about 90 percent by weight of hydrophilic solvent, from about 5 to about 95 percent by weight of high molecular weight polyethylene glycol having a molecular weight of at least about 720 daltons, from about 1 to about 30 percent by weight of a $C_{14}$ to $C_{30}$ fatty alcohol, from about 1 to about 20 percent by weight of emulsifying surfactant having a combined HLB in a range greater than 7, from about 0.1 to about 30 percent by weight of natural fats or oils, from about 0.1 to about 10 percent by weight of sterols or sterol derivatives and from about 0.1 to about 10 percent by weight of emollient.

2. The absorbent article of claim 1, wherein the composition has a melting point from about 32° C. to about 100° C.

3. The absorbent article of claim 1, wherein the composition has a viscosity of from about 200 to about 100,000 centipoise at a temperature of 55° C.

4. The absorbent article of claim 1, wherein the composition has a penetration hardness of from about 5 millimeters to about 365 millimeters at 25° C.

5. The absorbent article of claim 1, wherein the composition is on the bodyfacing surface in an amount of from about 0.1 grams per meter squared (g/m²) to about 30 g/m².

6. The absorbent article of claim 1, wherein the hydrophilic solvent of the composition is selected from water, propylene glycol, low molecular weight polyethylene glycol, glycerin, hydrogenated starch hydrolysate and mixtures thereof.

7. The absorbent article of claim 1, wherein the molecular weight of the high molecular weight polyethylene glycol is from about 720 to about 1,840,000 daltons.

8. The absorbent article of claim 1, wherein the molecular weight of the high molecular weight polyethylene glycol is from about 1,400 to about 440,000 daltons.

9. The absorbent article of claim 1, wherein the fatty alcohol of the composition is selected from cetyl alcohol, stearyl alcohol, arachidyl alcohol, behenyl alcohol and mixtures thereof.

10. The absorbent article of claim 1, wherein the surfactant of the composition is selected from glyceryl stearate SE, glycol stearate SE, sorbitan stearate, water dispersible metal soaps, lauryl methicone copolymers, cetyl methicone copolymers, cetyl dimethicone copolymers, stearyl dimethicone copolymers, behenyl dimethicone copolymer, dimethicone copolymers and mixtures thereof.

11. The absorbent article of claim 1, wherein the natural fat or oil of the composition is selected from Avocado Oil, Apricot Oil, Babassu Oil, Borage Oil, Camellia Oil, Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Benenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

12. The absorbent article of claim 1, wherein the stero or sterol derivative of the composition is selected from cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, sterol esters and mixtures thereof.

13. The absorbent article of claim 1, wherein the emollient of the composition is selected from petroleum based oils, petrolatum, mineral oils, alkyl dimethicones, alkyl methicones, phenyl silicones, alkyl trimethylsilanes, dimethicone, lanolin, fatty alcohols and mixtures thereof.

14. The absorbent article of claim 1, wherein the composition further includes from about 1 to about 20 percent by weight of a viscosity enhancer.

15. The absorbent article of claim 14, wherein the viscosity enhancer is selected from actrylamides copolymers, agar, gelatin, water dispersible metal soaps, butoxy chitosan, carboxymethyl cellulose, hydrated silica, kelp, magnesium silicate, methyl cellulose, PEG crosspolymer, polyvinyl alcohols, sodium acrylates copolymers, TEA alginates, xanthan gums, yeast polysaccharides and mixtures thereof.

16. The absorbent article of claim 1, wherein the composition further includes a water-based emulsion containing dimethicone.

17. The absorbent article of claim 1, wherein the composition further includes a microencapsulated dimethicone.

18. The absorbent article of claim 1, wherein the composition further includes an entrapped dimethicone.

19. The absorbent article of claim 1, wherein the composition further includes a dimethicone-treated powder.

20. A method of applying a composition to a bodyfacing surface of a bodyside liner of an absorbent article comprising the steps of:
  (a) heating a composition comprising a hydrophilic solvent, a high molecular weight polyethylene glycol having a molecular weight of at least 720 daltons, a $C_{14}$ to $C_{30}$ fatty alcohol, an emulsifying surfactant having a combined HLB in a range greater than 7, natural fats or oils, a sterol or sterol derivative and an emollient to a temperature above the melting point of the composition, the composition having a melting point of from about 32° C. to about 100° C.;
  (b) applying the composition to the bodyfacing surface of a bodyside liner of an absorbent article; and
  (c) resolidifying the composition.

21. The method of claim 20, wherein after the step of resolidification, the composition has a viscosity of greater than about 200 centipoise.

22. The method of claim 20, wherein after the step of resolidification, the composition has a penetration hardness of from about 5 to about 365 millimeters at 25° C.

23. The method of claim 20, wherein after the step of heating, the composition is applied by spraying.

24. The method of claim 20, wherein after the step of heating, the composition is applied by slot coating.

25. The method of claim 20, wherein after the step of heating, the composition is applied by printing.

26. A composition comprising from about 10 to about 90 percent by weight of hydrophilic solvent, from about 5 to about 95 percent by weight of high molecular weight polyethylene glycol having a molecular weight of at least 720 daltons, from about 1 to about 30 percent by weight of a $C_{14}$ to $C_{30}$ fatty alcohol, from about 1 to about 20 percent by weight of emulsifying surfactant having a combined HLB in a range greater than 7, from about 0.1 to about 30 percent by weight of natural fat or oil, from about 0.1 to about 10 percent by weight of sterols and sterol derivatives and from about 0.1 lo about 10 percent by weight of emollient, wherein the composition has a penetration hardness of from about 5 to about 365 millimeters at 25° C.

27. The composition of claim 26, wherein the composition has a melting point from about 32° C. to about 100° C.

28. The composition of claim 26, wherein the composition has a process viscosity less than about 100 centipoise under shear and pressure.

29. The composition of claim 26, wherein the composition further includes a dimethicone-treated powder.

30. The composition of claim 26, wherein the hydrophilic solvent of the composition is selected from water, propylene glycol, low molecular weight polyethylene glycol, glycerin, hydrogenated starch hydrolysate and mixtures thereof.

31. The composition of claim 26, wherein the molecular weight of the high molecular weight polyethylene glycol is from about 720 to about 1,840,000 daltons.

32. The composition of claim 26, wherein the molecular weight of the high molecular weight polyethylene glycol is from about 1,400 to about 440,000 daltons.

33. The composition of claim 26, wherein the fatty alcohol of the composition is selected from cetyl alcohol, stearyl alcohol, arachidyl alcohol, behenyl alcohol and mixtures thereof.

34. The composition of claim 26, wherein the surfactant of the composition is selected from glyceryl stearate SE, glycol stearate SE, sorbitan stearate, water dispersible metal soaps, lauryl methicone copolymers, cetyl methicone copolymers, cetyl dimethicone copolymers, stearyl dimethicone copolymers, behenyl dimethicone copolymer, dimethicone copolymers and mixtures thereof.

35. The composition of claim 26, wherein the natural fat or oil is selected from Avocado Oil, Apricot Oil, Babassu Oil, Borage Oil, Camellia Oil. Canola Oil, Castor Oil, Coconut Oil, Corn Oil, Cottonseed Oil, Evening Primrose Oil, Hydrogenated Cottonseed Oil, Hydrogenated Palm Kernel Oil, Maleated Soybean Oil, Meadowfoam Oil, Palm Kernel Oil, Peanut Oil, Rapeseed Oil, Safflower Oil, Sphingolipids, Sweet Almond Oil, Tall Oil, Lauric Acid, Palmitic Acid, Stearic Acid, Linoleic Acid, Stearyl Alcohol, Lauryl Alcohol, Myristyl Alcohol, Benenyl Alcohol, Rose Hip Oil, Calendula Oil, Chamomile Oil, Eucalyptus Oil, Juniper Oil, Sandlewood Oil, Tea Tree Oil, Sunflower Oil, Soybean Oil and mixtures thereof.

36. The composition of claim 26, wherein the sterol and sterol derivative is selected from cholesterol, sitosterol, stigmasterol, and ergosterol, as well as, $C_{10}$–$C_{30}$ cholesterol/lanosterol esters, cholecalciferol, cholesteryl hydroxystearate, cholesteryl isostearate, cholesteryl stearate, 7-dehydrocholesterol, dihydrocholesterol, dihydrocholesteryl octyldecanoate, dihydrolanosterol, dihydrolanosteryl octyldecanoate, ergocalciferol, tall oil sterol, soy sterol acetate, lanasterol, soy sterol, avocado sterols, sterol esters and mixtures thereof.

37. The composition of claim 26, wherein the emollient of the composition is selected from petroleum based oils, petrolatum, mineral oils, alkyl dimethicones, alkyl methicones, phenyl silicones, alkyl trimethylsilanes, dimethicone, lanolin, fatty alcohols and mixtures thereof.

38. The composition of claim 26, wherein the composition further includes from about 1 to about 20 percent by weight of a viscosity enhancer.

39. The composition of claim 38, wherein the viscosity enhancer is selected from actrylamides copolymers, agar, gelatin, water dispersible metal soaps, butoxy chitosan, carboxymethyl cellulose, hydrated silica, kelp, magnesium silicate, methyl cellulose, PEG crosspolymer, polyvinyl alcohols, sodium acrylates copolymers, TEA alginates, xanthan gums, yeast polysaccharides and mixtures thereof.

40. The composition of claim 26, wherein the composition further includes a water-based emulsion containing dimethicone.

41. The composition of claim 26, wherein the composition further includes a microencapsulated dimethicone.

42. The composition of claim 26, wherein the composition further includes an entrapped dimethicone.

43. A method for enhancing skin barrier function on a skin surface of a user, comprising the steps of:
  a) contacting the skin surface of the user with a bodyfacing surface of a liner material, the bodyfacing surface having a composition comprising a hydrophilic solvent, a high molecular weight polyethylene glycol having a molecular weight of at least 720 daltons, a $C_{14}$–$C_{30}$ fatty alcohol, an emulsifying surfactant having a combined HLB in a range greater than 7, natural fat or oil, a sterol or sterol derivative and an emollient;
  b) maintaining the bodyfacing surface in contact with the skin surface for a sufficient amount of time to transfer the composition to the skin surface; and
  c) repeating the contact of the skin surface with the bodyfacing surface of the liner material for a sufficient period of time to enhance skin barrier function,
wherein the composition comprises from about 10 to about 90 percent by weight of hydrophilic solvent, from about 5 to about 95 percent by weight of high molecular weight polyethylene glycol having a molecular weight of at least 720 daltons, from about 1 to about 30 percent by weight of a $C_{14}$ to $C_{30}$ fatty alcohol, from about 1 to about 20 percent by weight of emulsifying surfactant having a combined HLB in a range greater than 7, from about 0.1 to about 30 percent by weight of natural fat or oil, from about 0.1 to about 10 percent by weight of sterols and sterol derivatives and from about 0.1 to about 10 percent by weight of emollient.

44. An absorbent article comprising:
  (a) an outer cover;
  (b) a liquid permeable bodyside liner that defines a bodyfacing surface and that is connected in superposed relation to the outer cover;
  (c) an absorbent body that is located between the bodyside liner and the outer cover; and a composition on at least a portion of the bodyfacing surface of the bodyside liner that includes from about 10 to about 90 percent by weight of hydrophilic solvent, from about 5 to about 95 percent by weight of high molecular weight polyethylene glycol having a molecular weight of at least about 720 daltons, from about 1 to about 30 percent by weight of a $C_{14}$ to $C_{30}$ fatty alcohol, from about 1 to about 20 percent by weight of emulsifying surfactant having a combined HLB in a range greater than 7, from about 0.1 to about 30 percent by weight of natural fats or oils, from about 0.1 to about 10 percent by weight of sterols or sterol derivatives and from about 0.1 to about 10 percent by weight of emollient, wherein the composition has a viscosity of from about 200 to about 100,000 centipoise at a temperature of 55° C.

45. An absorbent article comprising:
  (a) an outer cover;
  (b) a liquid permeable bodyside liner that defines a bodyfacing surface and that is connected in superposed relation to the outer cover;
  (c) an absorbent body that is located between the bodyside liner and the outer cover; and a composition on at least a portion of the bodyfacing surface of the bodyside liner that includes from about 10 to about 90 percent by weight of hydrophilic solvent, from about 6 to about 95 percent by weight of high molecular weight polyethylene glycol having a molecular weight of at least about 720 daltons, from about 1 to about 30 percent by weight of a $C_{14}$ to $C_{30}$ fatty alcohol, from about 1 to about 20 percent by weight of emulsifying surfactant having a combined HLB in a range greater than 7, from about 0.1 to about 30 percent by weight of natural fats or oils, from about 0.1 to about 10 percent by weight of sterols or sterol derivatives and from about 0.1 to about 10 percent by weight of emollient, wherein the composition has a penetration hardness of from about 5 millimeters to about 365 millimeters at 25° C.

* * * * *

UNITED STATES PATENT AND TRADEMARK OFFICE
CERTIFICATE OF CORRECTION

PATENT NO.    : 6,756,520 B1
DATED         : June 29, 2004
INVENTOR(S)   : Duane Gerard Krzysik et al.

It is certified that error appears in the above-identified patent and that said Letters Patent is hereby corrected as shown below:

Column 39,
Line 19, delete "stero" and substitute -- sterol --.

Column 40,
Line 22, delete "lo" and substitute -- to --.

Column 42,
Line 38, delete "6" and substitute -- 5 --.

Signed and Sealed this

Seventeenth Day of May, 2005

JON W. DUDAS
*Director of the United States Patent and Trademark Office*